(12) United States Patent
Remacle et al.

(10) Patent No.: US 7,396,643 B2
(45) Date of Patent: Jul. 8, 2008

(54) METHOD FOR THE SCREENING, THE DETECTION AND/OR THE QUANTIFICATION OF TRANSCRIPTIONAL FACTORS

(75) Inventors: José Remacle, Malonne (BE); Patricia Renard, Lonzee (BE); Muriel Art, Namur (BE)

(73) Assignee: Eppendorf Array Technologies, S.A., Namur (BG)

( * ) Notice: Subject to any disclaimer, the term of this patent is extended or adjusted under 35 U.S.C. 154(b) by 3 days.

(21) Appl. No.: 09/816,763

(22) Filed: Mar. 23, 2001

(65) Prior Publication Data
US 2002/0110814 A1   Aug. 15, 2002

(30) Foreign Application Priority Data
Mar. 24, 2000   (EP) ................................. 00870057

(51) Int. Cl.
*C12Q 1/68* (2006.01)
(52) U.S. Cl. ............................................. 435/6; 435/6
(58) Field of Classification Search .................... 435/6, 435/254.11, 325, 462, 70.1, 320.1, 7.1, 7.5, 435/7.72, 35; 536/23.1, 23.2, 23.4; 530/350, 530/388.21
See application file for complete search history.

(56) References Cited

U.S. PATENT DOCUMENTS

| 4,968,602 | A | * | 11/1990 | Dattagupta | ................. | 435/6 |
| 5,563,036 | A | | 10/1996 | Peterson et al. | | |
| 5,747,253 | A | | 5/1998 | Ecker et al. | | |
| 5,770,722 | A | * | 6/1998 | Lockhart et al. | ............ | 536/25.3 |
| 5,846,683 | A | | 12/1998 | Murakami et al. | | |
| 5,939,261 | A | | 8/1999 | Loewy et al. | | |
| 5,976,795 | A | * | 11/1999 | Voytas et al. | .................. | 435/6 |
| 6,326,489 | B1 | | 12/2001 | Church et al. | | |
| 6,342,353 | B1 | * | 1/2002 | Heslot et al. | .................. | 435/6 |
| 2002/0115198 | A1 | * | 8/2002 | Nerenberg et al. | ........ | 435/287.2 |

FOREIGN PATENT DOCUMENTS

| EP | 0620439 A2 | 4/1994 |
| WO | WO 89/11548 | 11/1989 |
| WO | WO 95/30026 | 11/1995 |
| WO | WO 98/03652 | 1/1998 |
| WO | WO 98/08096 | 2/1998 |
| WO | WO 00/22167 | 4/2000 |

OTHER PUBLICATIONS

Brand et al., "Activated Transcription FActor Nuclear Factor-Kapa B is Present in the Atherosclerotic Lesion," Journal of Clinical Investigation, APr. 1996, vol. 97, No. 7, pp. 1715-1722.*
Guo, Z., et al., (1994) Direct fluorescence analysis of genetic polymorphisms by hybridization with oligonucleotide arrays on glass supports. Nucleic Acids Research 22:5456-5465.
Hibma, M., et al., (1994) A non-radioactive assay for the detection and quantitation of a DNA binding protein. Nucleic Acids Research 22:3806-3807.
Anthony, R.M., et al., (2000) Rapid Diagnosis of Bacteremia by Universal Amplification of 23S Ribosomal DNA Followed by Hybridization to an Oligonucleotide Array. J. Clinical Microbio. (No. 2) 38: 781-788.
Zammatteo, N., et al., (1997) Comparison between microwell and bead supports for the detection of human cytomegalovirus amplicons by sandwich hybridization. Anal. Biochem. 253: 180-189.
European Search Report, from Priority Application EP 00870057 dated Sep. 14, 2000.
Baeuerle et al., Advances in Immunology, *NF-κB as a Frequent Target for Immunosuppressive and Anti-Inflammatory Molecules*, vol. 65 (1997), pp. 111-137.
Benotmane et al., Analytical Biochemistry, *Nonisotopic Quantitative Analysis of Protein-DNA Interactions at Equilibrium*, vol. 250, (1997) pp. 181-185.
Gubler et al., BioTechniques, *Nonradioactive Assay for Sequence-Specific DNA Binding Proteins*, vol. 18, No. 6 (1995) pp. 1008, 1011-1014.
Schreck et al., Nucleic Acids Research, *The NF-κB transcription factor induces DNA bending which is modulated by its 65-kD subunit*, vol. 18, No. 22 (1990), pp. 6497-6502.
Yi et al., Biochemistry, *Divalent Cations Stimulate Preferential Recognition of a Viral DNA End by HIV-1 Integrase*, vol. 38, No. 26 (1999), pp. 8458-8468.
Zabel et al., EMBO Journal, *Nuclear uptake control of NF-κB by MAD-3, an IκB protein present in the nucleus*, vol. 12, No. 1 (1993) pp. 201-211.
Bielinska, A. et al., "Regulation of Gene Expression with Double-Stranded Phosphorothioate Oligonucleotides," Science 250:997-1000 (1990).
Brivanlou, A. et al., "Signal Transduction and the Control of Gene Expression," Science, 295:813-818 (2002).
Ghosh, I. et al., "Structure-Function Relationship in a 3-Sheet Peptide Inhibitor of E47 Dimerization and DNA Binding," *Bioorg. & Med. Chem.* 7:61-66 (1999).

(Continued)

*Primary Examiner*—Young J Kim
(74) *Attorney, Agent, or Firm*—Knobbe, Martens, Olson & Bear LLP

(57) ABSTRACT

The present invention is related to a screening, detection and/or quantification method of one or more transcriptional factor(s) (1) possibly present in a biological sample, said method comprising the steps of:
  possibly extracting and isolating said transcriptional factor (1) from said biological sample,
  putting into contact the transcriptional factor (1) with a double-stranded DNA sequence (2) bound to an insoluble solid support (3), and
  detecting and/or quantifying said fixed transcriptional factor (1),
said double-stranded DNA sequence having a specific sequence able to be fixed by the transcriptional factor (1) and being preferably located at a distance of at least about 6.8 nm from the surface of the solid support (3), and said double-stranded DNA sequence being bound to the surface of the insoluble solid support (3) at a concentration of at least 0.01 pmole/cm$^2$ of solid support surface (3).

Figure 1:
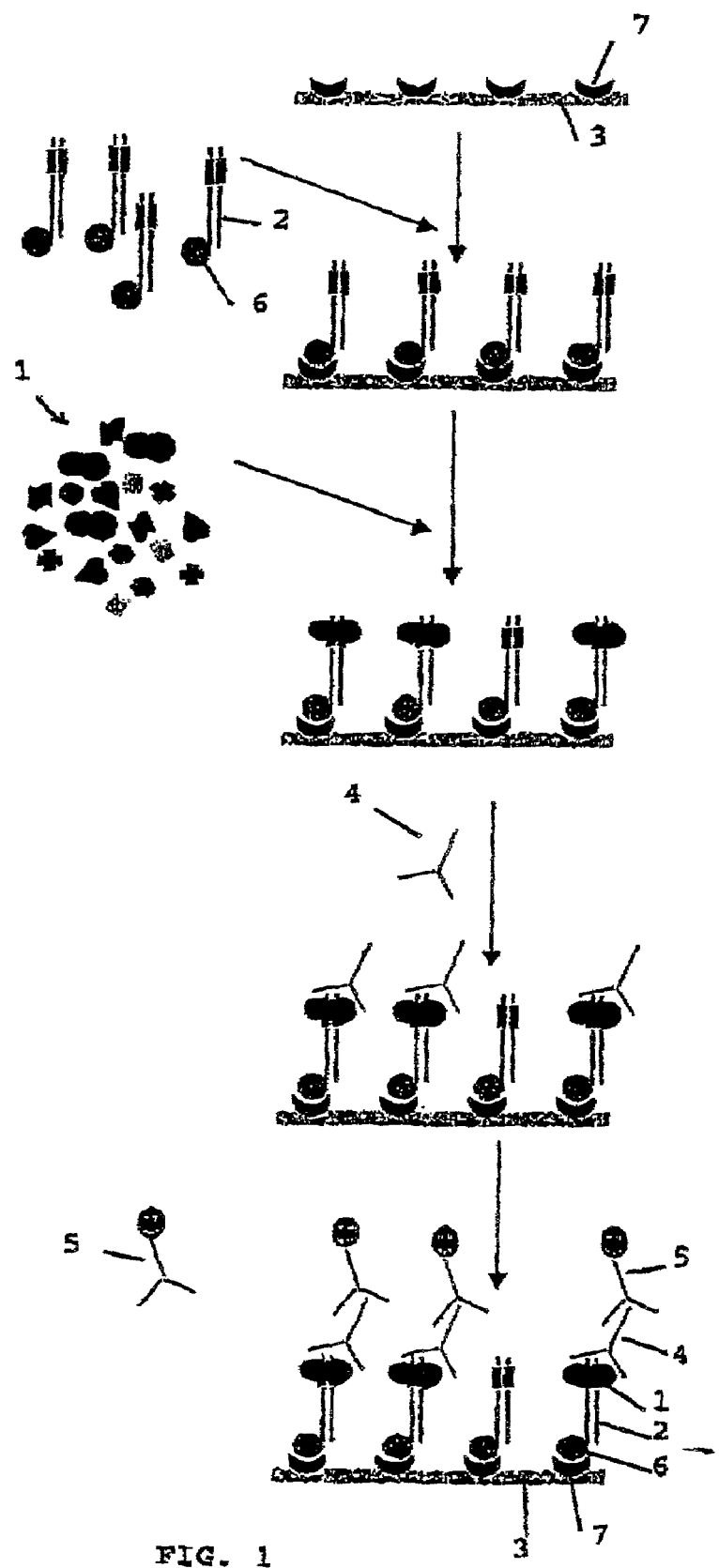

The present invention is also related to the kit comprising means and media for performing said method.

22 Claims, 5 Drawing Sheets

OTHER PUBLICATIONS

Grigoriev, M. et al., "Inhibition of Gene Expression by Triple Helix-Directed DNA Cross-Linking at Specific Sites," *PNAS USA* 90:3501-3505 (1993).

Nielsen, P. et al., "Sequence-Selective Recognition of DNA by Strand Displacement with a Thymine-Substituted Polyamide," *Science* 254:1497-1500 (1991).

Tanaka, H. et al., "Sequence-specific interaction of a ∀∃-anomeric double-stranded DNA with the p50 subunit of NFιB: application to the decoy approach," *Nucleic Acids Research* 22:3069-3074 (1994).

Yao, S. et al., "Uncoiling c-Jun Coiled Coils: Inhibitory Effects of Truncated Fos Peptides on Jun Dimerization and DNA Binding In Vitro," *Biopolymerics* 47:277-283 (1998).

Ghiorzo, P. et al. (1997) "c-Rel and p65 subunits bind to an upstream NF-κB site in human granulocyte macrophage-colony stimulating factor promoter involved in phorbol ester response in 5637 cells" *FEBS Letters* 418:215-218.

Kaltschmidt, C. et al. (1995) "Selective recognition of the activated for of transcription factor NF-xB by a monoclonal antibody" *Biol. Chem. Hoppo-Seyler* 376:9-16.

* cited by examiner

METHOD FOR THE SCREENING, THE DETECTION AND/OR THE QUANTIFICATION OF TRANSCRIPTIONAL FACTORS

CROSS-REFERENCE TO RELATED APPLICATIONS

This application claims priority to European Application Serial Number 00870057.7 filed on Mar. 24, 2000, the disclosure of which is incorporated herein by reference in its entirety.

FIELD OF THE INVENTION

The present invention is related to a method and kit comprising reagents and media for the screening, the detection and/or the quantification of transcriptional factors or compounds binding said factors by non radioactive detection means.

BACKGROUND OF THE INVENTION

Transcriptional factors are proteins that bind to specific sequences of DNA, called consensus sequences, and influence the transcription of the DNA into mRNA. Some of these factors directly participate in the transcription process by activating or inhibiting the transcription and regulate the synthesis of proteins needed by cells to function, to adapt, to respond or to differentiate. Some of these proteins have to be transcribed in a constitutive manner (essential role in cell functions) while others are only synthesised in response to specific stimuli or when the cells are for instance in pathological environment. External signals are sensed by receptors and transduced through the plasma membrane followed by cascades of enzymatic kinase reactions, resulting in a phosphorylation or dephosphorylation of the transcriptional factors which affects positively or negatively their binding to their consensus sequence.

An example of drug acting indirectly on transcriptional factor is compactin, an inhibitor of HMG CoA reductase, which leads to an up-regulation of the transcription of the LDL receptor gene, permitting the clearance of cholesterol (U.S. Pat. No. 5,563,036).

DESCRIPTION OF THE RELATED ART

There is a need for the detection and quantification of transcriptional factors (working as regulators and adaptators) for improving the diagnostic of pathologies or for developing drug affecting their activity.

Several methods are currently used to estimate the activation of transcriptional factors like NFκB. The most common method is to assay for their DNA-binding capacity by gel retardation, also called electrophoretic mobility shift assay (EMSA) (Schreck, R. et al, *Nucleic Acids Res*, 18(22), 6497-502 (1990)). This method is sensitive, but does not allow the simultaneously processing of numerous samples and requires particular precautions and equipments necessary for the handling of radioactivity.

A second largely used method is based on reporter genes (luciferase or β-galactosidase genes) placed under the control of a promoter containing the consensus sequence. This promoter can be artificial, made of several specific cis-elements and a TATA box, or natural, like the HIV long terminal repeat (LTR) element. However, other transcription factors influence the expression level of the reporter gene. In addition, as the read-out is the enzymatic activity of luciferase, for instance, the results may be affected by interferences with downstream processes like general transcription or traduction machinery. This method is widely used provided the cells are efficiently transfected with the reporter plasmid.

Two other indirect methods are restricted to a few transcription factors. The first one uses antibodies raised specifically against the nuclear localising sequence (NLS) of transcriptional factors like NFκB, a part of the protein which is masked by IκB when the transcription factor is inactivated (Zabel, U. et al., *EMBO J.*, 12(1), 201-211 (1993)). The activation of NFκB can be visualised by immunofluorescence with this antibody. This method does not suit many samples analysis.

These various methods have been very helpful for fundamental research during these last 10 years, to unravel the molecular activation mechanisms of transcriptional factors like NFκB or AP1. Nevertheless, research has been hampered in this field by the fact that no convenient assay suitable for large scale screening procedure was available.

An assay for testing the inhibition by pharmacological agents of transcriptional factors binding to their specific sequence has been described in the patent U.S. Pat. No. 5,563,036. The potentially active agent is incubated with the radioactively labelled transcriptional factor and the inhibition of its binding to the specific sequence is then assayed. This sequence is conjugated to biotin capable of specific binding to avidin immobilised onto microwells. A factor bound to the sequence and bearing biotin will be captured by avidin-coated plates and measured. The labelled protein, the nucleic acid conjugate and the compound form a mixture that is incubated with the avidin immobilised on the solid substrate. The binding of the factor to its sequence is performed in solution for testing possible inhibition by a pharmaceutical agent present in solution.

In solution, the length of the nucleic acid probe ranges between 28 and 60 base pairs. This assay works with high concentration of factor in solution, but it is not at all sensitive for diagnostic assay in biological samples. Furthermore, probe excess has to be added in solution. The probe, which binds to avidin on the support, is preferably a free probe which has a smaller size and thus a much higher diffusion rate, so that the level of binding of probe/factor complex is low.

The U.S. Pat. No. 5,747,253 describes a method for the identification of oligomers having a very high specific binding capacity for transcriptional factors. Synthesised oligonucleotides are first incubated with factors in solution in order to test their binding affinity to the factor, then assayed by attaching the oligonucleotide up to 25 bases to a support through a linker moiety present on the oligonucleotides. The reaction between the factor and the oligonucleotide is performed in solution, thereby limiting the sensitivity.

Magnetic microparticles can also be used to capture complexes formed between nucleic acids and proteins as proposed in document U.S. Pat. No. 5,939,261. The reaction is performed in solution thus leading to the already mentioned limitations.

Gubler and Abarzua (Biotechniques, 18, 1008, 1011-4 (1995)) describe immobilised antibodies on the surface of wells to capture the transcriptional factor present in a solution. A biotinylated probe is added in the solution so that the active factors will be immobilised together with their probes that can then be detected with alkaline-phosphatase-streptavidin conjugate. However, all transcriptional factors either active or not will bind to the antibodies. There will be a competition for the binding to the antibodies. Results on cell extracts showed a sensitivity of 2 μg in the assay for the p53 protein.

Benotmane et al (Analytical Biochemistry 250, 185-185 (1997)) describe a protein-DNA binding of a recombinant protein at equilibrium, said recombinant protein, a fragment 6D3 of HLTF, having a DNA binding domain, the 6D3 portion of an helicase, linked to the glutathione S-transferase (GST). The binding coefficient and the dissociation coefficient in two experimental systems are determined by testing the binding of the biotinylated probe on a protein onto wells surface, or binding of the protein onto a consensus sequence of 27 base pairs fixed to the wells surface. In both cases they detect the protein-DNA binding. However they found a lower dissociation constant in the second test. There was no attempt to test the method on cell extract and it is difficult to assess the real sensitivity of the method given the fact that pure recombinant protein was used in this assay.

In cells or tissues, the transcriptional factors are present in minute amounts and this is the reason why the EMSA based on the incubation of the large excess of radioactive labelled probes in solution is the standard assay in the laboratories. In many cases, the concentration of the transcriptional factor is below the dissociation constant since the factors are diluted during the preparation of cell lysates. For this reason, an excess of probes allows the displacement of the binding reaction towards the formation of the DNA-protein complex. Secondly the low level of binding can be detected due to the high sensitivity of the $P^{32}$ radioactive measurement. These difficulties explain also why alternative assays also use radioactive labelling or are only valid when performed on purified proteins.

SUMMARY OF THE INVENTION

The present invention aims to provide a new and improved method and device for the screening, the detection (and possibly the quantification) of transcriptional factors or compounds binding said factors, preferably several of them being present in a biological sample, preferably by using non radioactive detection means.

Definition

Tranceriptional factors are proteins which bind to specific sequences of double stranded DNA, called consensus sequences, and when activated either by themselves or with the help of other proteins or enzymes will modulate, either activate or repress, the transcription of the DNA.

The transcriptional factors are usually found in both active or inactive forms, the shift form one form to the other being usually reversible. They are composed of a DNA binding domain and a transactivating domain responsible for their activity and they can be part of a large protein complex which interacts with the transcriptional machinery for regulating its activity.

The following method according to the invention may also be used for the screening, detection and/or quantification of proteins which bind to specific double stranded DNA. One such protein is the HIV integrase which recognises the sequence 5'-GTGTGGAAAATCTCTAGCA-3' (SEQ ID NO:132) with a possible GT at the 3' end which is cut by the enzyme. The enzyme can be stabilised in its binding form using specific experimental conditions mainly the presence of Me++ (Yi et al. Biochemistry 38, 8458, 1999). Other viral proteins binding to DNA sequence are listed in table 1 and are also possibly detected by the present invention.

DETAILED DESCRIPTION OF THE PREFERRED EMBODIMENTS

The present invention is related to a screening and/or quantification method of one or more transcriptional factor(s) 1 present in a cell or a cell lysate (including nuclear lysate of a cell), said method described in the enclosed FIG. 1 comprising the steps of:

binding to an insoluble solid support 3, double-stranded DNA sequence(s) 2 at a concentration of at least about 0.01 pmole/cm², preferably 0.1 pmole/cm², of said solid support surface (step 1), said double-stranded DNA sequence 2 further comprising a specific nucleotide sequence able to bind specifically said transcriptional factor(s) 1, putting into contact said transcriptional factor(s) 1 with said bound double-stranded DNA sequence(s) 2, and identifying and/or quantifying a signal resulting from the binding of said transcriptional factor(s) 1 to said double-stranded DNA sequence(s) 2.

Preferably, said signal is obtained by the following step:

after washing, the presence of the fixed transcriptional factor 1 is detected by using firstly a primary antibody 4 raised against the factor 1 (step 2) and then a secondary labelled antibody 5 (for example conjugated with an enzyme such as peroxidase) directed against the primary antibody 4 (step 3).

The presence of the peroxidase is then advantageously assayed through the addition of a suitable substrate by a colorimetric detection of the reaction product in solution (step 4). Such non-radioactive method is rapid, more sensitive than gel retardation, and suits for large-scale screening or detection upon various solid supports.

It is meant by "a specific nucleotide sequence of a double-stranded DNA sequence able to bind a transcriptional factor", a nucleotide sequence which can be recognised specifically through biochemical interactions by said transcriptional factor(s).

The present invention is sensitive enough to be applied for the detection of transcriptional factors or proteins able to bind DNA sequence present in cell lysate (including nuclear lysate) or present in a body fluid. Unexpectedly, less than about $10^{-12}$ mole of transcritional factor can be detected in 50 micro-litres in an assay using the method of the present invention and the limit of detection was found to be of about 5.10-16 mole for NF-KB assay. This sensitivity explains the possibility of using such invention for the detection of transcriptional factors naturally present in cell lysate. The sensitivity obtained which is at least as good as the EMSA method (example 2), is a surprising finding since the DNA consensus is not in solution, but fixed on (bound to) a solid surface (where the reaction is slower than in solution) and the detection does not require the radioactive measurement but may be obtained by simple colorimetry.

Preferably, in the method according to the invention, the specific nucleotide sequence of the double-stranded DNA sequence(s) able to bind with the transcriptional factor(s) is located at a distance of at least 6.8 nm from the surface of the solid support.

According to a preferred embodiment of the present invention, the double-stranded DNA sequence may comprise a spacer of at least about 13.5 nm between the specific sequence and the surface of the solid support.

Preferably, said spacer is a double-stranded DNA nucleotide sequence of at least 20 base pairs, preferably at least 50, 100, 150 or 250 base pairs.

Another aspect of the present invention is related to a screening, diagnostic and/or quantification kit comprising means and media for performing the method according to the invention.

Preferably, the invention is related also to a screening and/or quantification kit or device including high throughput screening device, possibly comprising computer-controllable electromagnetic means and robots (such as high-throughput screening device) allowing the screening and detection upon any type of solid support 1 and used for the screening and/or quantification of transcriptional factor(s) (or compounds able to bind said transcriptional factor(s) or inhibit the binding of said transcriptional factor) to said specific nucleotide sequence comprised in the double-stranded DNA bound to the insoluble solid support at a concentration of at least about 0.01 pmole/cm$^2$ of solid support surface; said specific nucleotide sequence being located at a distance of at least about 6.8 nm from the surface of the solid support.

The screening and/or quantification kit according to the invention comprises also means and media for detecting the signal resulting from the binding of the transcriptional factor(s) to the double-stranded DNA sequence(s), said signal being a non-radioactive resulting signal.

The method and kit according to the invention is also suitable for the (possibly simultaneous) screening and/or quantification of multiple different transcriptional factors present in a same biological sample (cell or cell lysate). The method is especially well adapted for the detection of multiple transcriptional factors, on a same support (one biochips or one multiwell plate). However, the detection of the different factors from a same sample can also be performed in wells of different plates.

The method according to the invention may comprise also the step of screening and/or quantifying compound(s) able to bind to said transcriptional factor(s) (or inhibit their binding) to the specific sequence, preferably by using steps, means and media such as the ones described in the U.S. Pat. No. 5,563,036.

The method according to the invention may also comprise the step of identification of at least one characteristic specific of a given transcriptional factor activation. Some transcriptional factors can bind to their consensus DNA sequence without activating the transcriptional machinery. The activation is then associated with one or several specific changes, the most common one being the phosporylation (or dephosphorylation) at specific amino acid(s) of the protein. An example of such transcriptional factor is CREB, which is only active when phosphorylated (example 1).

The method according to the invention may also comprise the step of screening and/or quantifying known and unknown compound(s) able to modulate the activation of said transcriptional factor(s) in cells, tissues or organisms and detecting the residual activity of the transcriptional factor(s) in cell lysate. External protein having at least in part the binding DNA domain can also be added to the incubation solution in order to determine its possible activation by cell lysate and to obtain a screening of compounds acting upon this activation. If a purified trancriptional factor is added to the cell lysate, its activation can be quantified by determination of one or several of its specific characteristics. Proteins acting as activators or inhibitors upon a transcriptional factor activation can also be added in the incubation medium and serve in a screening method of compounds acting upon these proteins.

The method may also comprise the step of forming a mixture by combining a labelled protein comprising a portion of the transcriptional factor with the specific nucleotide sequence being bound to the insoluble solid support. Thereafter, the method comprises the step of incubating said mixture in the conditions, whereby in the absence of the compound, the labelled protein binds to the nucleotide sequence, the step of separating from the solid support a fraction of said mixture, whereby the fraction comprises the labelled protein if said labelled protein is not bound to the sequence and the step of detecting the presence or absence of said labelled protein upon said solid support; wherein the absence of said detected label upon said solid support, means that the compound inhibits the binding of a transcriptional factor to the nucleotide sequence. Preferably, said method comprises also the step of recovering the detected unknown compound.

According to the invention, the solid support is preferably an array bearing at least 4, 10, 16, 25, 100, 1000, 10.000 or more spot/cm$^2$ of solid support surface, each spot containing at a specific location double-stranded DNA sequence(s) for the binding of transcriptional factor(s).

According to a preferred embodiment of the present invention, the double-stranded DNA sequence 2 is bound to a first member 6 of a binding pair such as biotin/streptavidin, hapten/receptor, antigen/antibody), able to interact with the second member 7 of said binding pair, bound to the surface of the solid support 3.

Alternatively, the double-stranded DNA sequence(s) could be covalently bound to the surface of the insoluble solid support.

Alternatively, the method according to the invention could comprise also the step of identification of transcriptional factor(s) and/or protein(s) which are part of their active complex.

The method according to the invention may also comprise the step of screening or detecting the "fixed" transcriptional factor(s) and possibly quantifying the presence of said "fixed" transcriptional factor(s) (and/or possibly quantifying the concentration of the trancriptional factor(s) present in a biological sample (cell or cell lysate)).

The use of a consensus DNA sequence 2 already fixed on a solid support 3 allows the industrial production with reproducible and quality control of the kit or device containing such prepared support. It also simplifies the use of the kit since a biological sample (cell or cell lysate) can be incubated directly upon such prepared solid support surface without requiring the addition of any other reagent.

Said general method for detecting the DNA-binding capacity of transcriptional factors is enough sensitive, specific and valid for most (if not all) transcription factors. Unexpectedly, it is possible to improve said sensitive method, by increasing the size of the spacer between a consensus sequence on which the transcriptional factor will bind and by using a very high density of these nucleotide sequences attached on the solid support surface. The method is so sensitive that it can be used for the detection of one factor present in a biological sample, but also for the detection of several factors by the use of multiple nucleotide sequences attached in distinctive spots on a solid surface such as biochips (microarrays).

The minimum spacer was found to be a nucleotide sequence, such as a DNA sequence, of 20 base pairs (bp), but said spacer may have between 50 and 250 base pairs according to the type of solid support and antibody used (Example 4). The presence of the consensus nucleotide sequence at long distance from the solid support surface can be obtained similarly through the presence of a chemical spacer of at least 10 atoms, preferably of at least 44 atoms, more preferably of at least 50 atoms or more.

Said method, kit or device are suitable for testing the activity of pharmaceutical drugs or methods acting upon these transcriptional factors (i.e. as inhibitors and/or activators of their binding to the DNA) or on their regulatory processes: activation or repression.

The invention is also related to said compound identified or recovered and possibly integrated in a pharmaceutical composition for preventing or treating various symptoms or diseases.

Said screening, detection and/or quantification method and kit are suitable for detection and quantification of all the transcriptional factors for which the DNA binding sequence is known. These transcriptional factors and their properties are listed in the TRANSFAC.gbf.de Web site in its The Transcription Factor DataBase. The most commonly tested factors are selected from the group consisting of NF-κB, AP-1, CREB, SP-1, C/EBP, GR, HIF-1, Myc, NF-AT, Oct, TBP and CBF-1. A list of some transcriptional factors and their corresponding consensus (sequences SEQ ID No. 1 to 125) is given in table 1.

NFκB is an important ubiquitous transcriptional factor activated following cell stimulation, involved in the immune response to some viral and bacterial products, oxidative stresses or pro-inflammatory cytokines (Baeuerle, P. A. and Baichwal, V. R., *Adv Immunol*, 65, 111-37 (1997)).

AP1 is also dimeric transcriptional factor which is involved in many cell responses through activation of kinase cascade. This transcription factor is involved in a variety of biological processes like cell growth, differentiation, or apoptosis.

Preferably, said detection and possibly quantification is obtained by the use of compounds that are able to specifically bind to the transcriptional factor fixed upon the double-stranded DNA, such as (preferably monoclonal) antibodies or specific hypervariable portions thereof (Fab', Fab2', etc.).

According to a preferred embodiment of the present invention, said binding is followed by incubation (and washing) with labelled compounds able to react with the first compound binding to said transcriptional factor, preferably (monoclonal) antibodies directed against the anti-transcriptional factor antibodies or specific hypervariable portions thereof (Fab', Fab2', etc.). Said last antibodies are preferably labelled with non radioactive markers allowing a detection, preferably by colorimetry, fluorescence, bioluminescence, electroluminescence or precipitation of a metal deposit (such as silver staining) as in example 3. Other secondary binding proteins like protein A which bind to antibodies are also an embodiment of the method. Said non radioactive test is preferably based upon a calorimetric assay resulting from an enzymatic activity such as described in the enclosed FIG. 1. If direct method such as mass spectrum analysis is sensitive enough it can be used for direct detection of the bound factor.

The selected antibody recognises an epitope which is accessible when the factor is in its active form and bound to DNA. Usually, the active and inactive forms of the factors differ in their phosphorylation state or by the presence of an inactivator protein. The antibody has to recognise the active form. The concentration of these transcription factors in a cell is very low and may reach the limit of the affinity coefficient of the antibodies. An antibody with a high affinity (i.e. with very low coefficient of dissociation) can highly increase the signal obtained. However, any other protein which has an affinity for the factor can be used for the detection.

Special applications are the use of specific antibodies directed against phospho-protein epitopes or against specific proteins which are part or can be attached to the transcriptional factor (see example 1). For NF-κB, antibodies directed either against P-50 or P-65 allow to determine the pattern of association of proteins giving the NF-κB activity.

The present invention also allows a differentiation between the DNA binding of the transcription factor and its activity. This activity is associated with one or several particular characteristics of the factors, the most common one being the phosphorylation at specific locations or the dissociation of inhibitory proteins. By using appropriate antibodies directed against these elements, it is possible to determine the amount of transcriptional factors in their active form. As an example, CREB can bind to its DNA consensus sequence without being active. Its activation results from a specific phosphorylation at a serine group, making the P-CREB. The present invention detects both the CREB binding and the P-CREB activation by using antibodies directed either against CREB or specific of the P-CREB (example 1).

The attached transcriptional factor can also be used to test for the presence of proteins which have affinity for the transcriptional factor.

The method comprises also the step of screening and/or quantifying known and unknown compound(s) able to modulate the activation of said transcriptional factor by modification of the level of specific characteristics of said factor.

If the binding is specific and if no other proteins are used on the nucleotide sequence binding on the surface, for example when the nucleotide sequences are directly linked to said surface, then a direct detection of protein will give an estimation and/or quantification of the bound factor.

A signal obtained in each well or for each spot of a biochip is recorded and the means of the signal are calculated for each identical consensus sequence. Usually, two (and preferably three to five) identical spots are present on each array in order to correct variations that may occur at any step of the process. The background values are wells or spots coated with a consensus sequence, in which binding buffer and lysis buffer is added instead of a cell extract or purified transcription factor (negative control). A positive control is preferably added as a factor obtained in a pure active form and for which a consensus nucleotide sequence is attached to the surface of the solid support in the test.

Quantification has to take into account not only for the binding yield, but also the detection part of the process and the reading scale. Internal or external standards using purified active transcriptional factor can be added to the sample at either step of the process in given amount as reference value to which the results will be compared. Validation of the use of these standards has to be performed earlier in order to validate their binding efficiency compared to the tested factors.

In the case of biological applications, comparison of transcriptional factors involved in the cell response can be quantified in comparison to transcriptional factors which are constitutively active (there are factors which regulate the expression of house keeping genes). The use of these "relative" quantification simplifies the assays, since all factors are treated in the same way during the various steps.

The simultaneous detection of several transcriptional factors binding or activity is especially usefull since it gives a pattern of response of the cells or tissues to a particular biological situation, to molecules or drug action. The transcriptional factors are activated by complex pathways which are related to each other. A general screening analysis of different transcriptional factors will give a better view and help the interpretation of the studied effects.

Furthermore, solid supports such as a biochips can be inserted in a machine support connected to another chamber and automatic machine through the control of liquid solution based upon the use of microfluidic technology. By being inserted into such a microlaboratory system, it can be incubated, heated, washed and labelled by automates, even for previous steps (like a PCR amplification) or the following step (labelling and detection). All these steps can be performed upon the same solid support.

According to the invention, the solid support is preferably selected from the group consisting of glass, metallic supports, polymeric supports (preferably a polystyrene support activated with carboxyl or amino groups present on its surface) or any other support used in the microchips (or micro-arrays) technology (preferably activated glass bearing aldehyde groups), said support comprising also specific coatings, markers or devices (bar codes, electronic devices, . . . ) for improving the assay.

If glass presents many advantages (like being inert and having a low auto-fluorescence), other supports like polymers, with various chemically well-defined groups at their surface, allowing the binding of the nucleotide sequences are useful.

Miniaturisation allows to perform one assay onto a surface (usually circular spots of about 0.1 to about 1 mm diameter). A low density array, containing 20 to 400 spots is easily obtained with pins of 0.25 mm at low cost. Higher density of spots going to 1,600 spots per cm2 can be obtained by reducing the size of the spots for example to 0.15 mm. The advantages of this technology is the high number of data which can be obtained and analysed simultaneously, the possibility to perform replicates and the small amount of biological sample necessary for the assay.

The arrays technology allows the simultaneous detection of different factors present in the same sample, which is possible due to the fact that several factors bind to their consensus sequence in the same reacting conditions. Solutions are available for example from Promega (Madison, Wis., USA) for the binding of several factors (Catalogue E3581). Conditions which allow the binding of the factors studied may be optimised by the person skilled in the art. Other binding assays involving DNA-DNA recognition, antigen-antibody or receptor-ligand recognition can be performed simultaneously on the same chips for other molecules.

The detection of the specific binding between the transcriptional factor and the double-stranded DNA sequence is obtained by any one of the methods described previously, or preferably by a method allowing a precipitation of a metal deposit (such as silver staining) at the location where the transcriptional factor has fixed (recognised) the double-stranded DNA sequence).

As only activated transcriptional factors are captured by the nucleotide sequences bound to the solid support (preferably microwell plates or microarray), the design of these sequences and binding conditions allow a very high sensitivity necessary for assays in biological samples.

The present invention will be described in more details in the following non limited examples in reference to the enclosed drawings.

SHORT DESCRIPTION OF THE DRAWINGS

FIG. 1 is a schematic presentation of the procedure for an assay or a transcriptional factor according to the invention.

Figure 2:
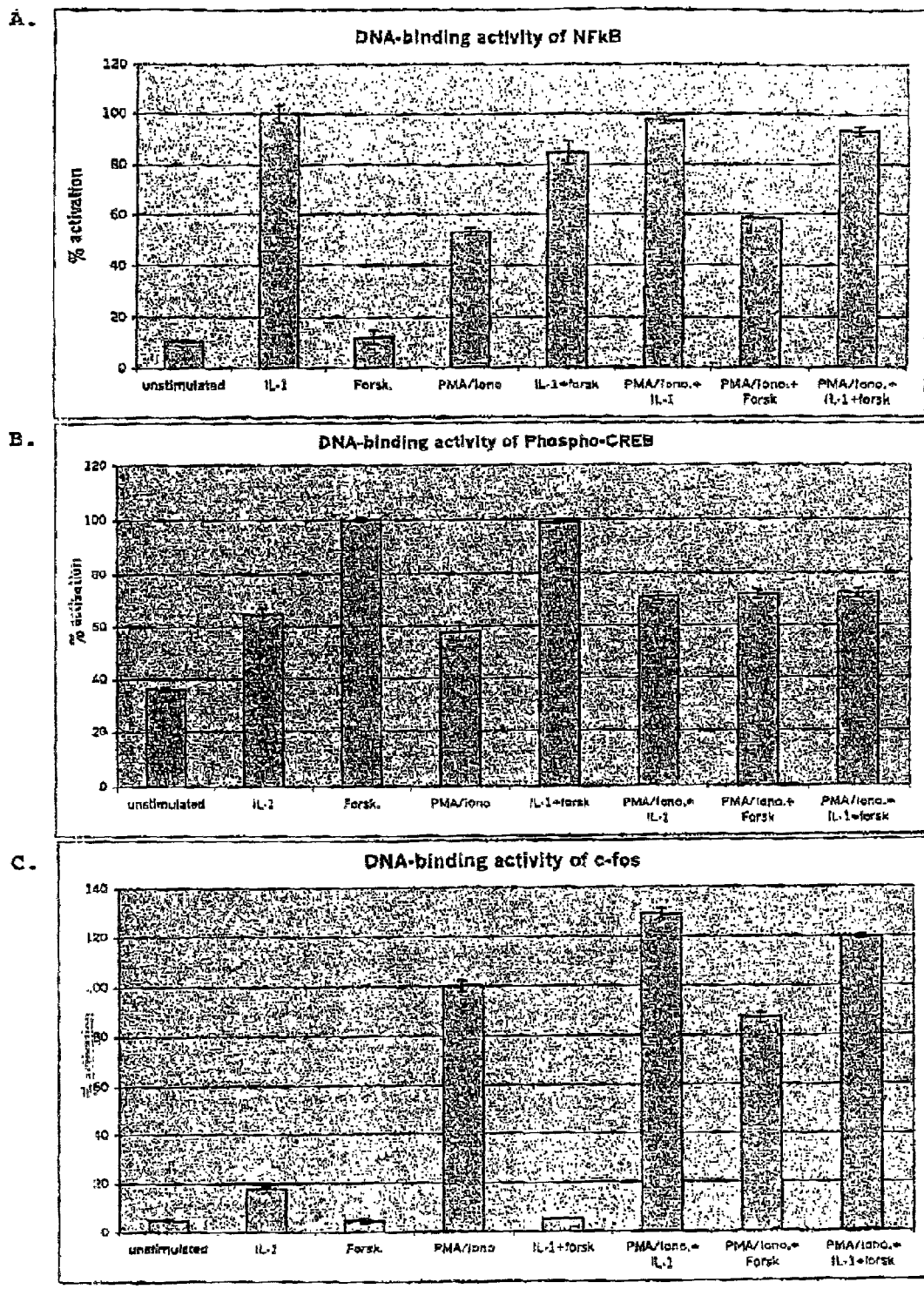

FIG. 2 represents a DNA-binding assay of 3 different transcription factors (NFκB, CREB and AP-1) measured simultaneously in the same cell extracts in microwells. Microwells contain a 100 bp DNA terminated by the sequence specific for either NFκB, CREB or AP-1, and the DNA binding capacity of the transcriptional is detected respectively with anti-p65, anti phospho-CREB and anti-c-fos (for AP-1 assay) The DNA-binding assay is performed on cell lysates coming either from cells left unstimulated, or stimulated with IL-1, with forskolin, with PMA+ionomycin, with IL-1 and forskolin, with IL-1 and PMA+ionomycin, with forskolin and PMA+ionomycin, and IL-1 and forskolin and PMA+ionomycin. The results show the signal obtained for the assay of NF-KB (A), P-CREB (B) and c-fos (C) on the various cell extracts (NF-KB is strongly induced in IL-1 stimulaued cells, P-CREB by forekolin scimulation and AP-1 by PNA)

Figure 3:
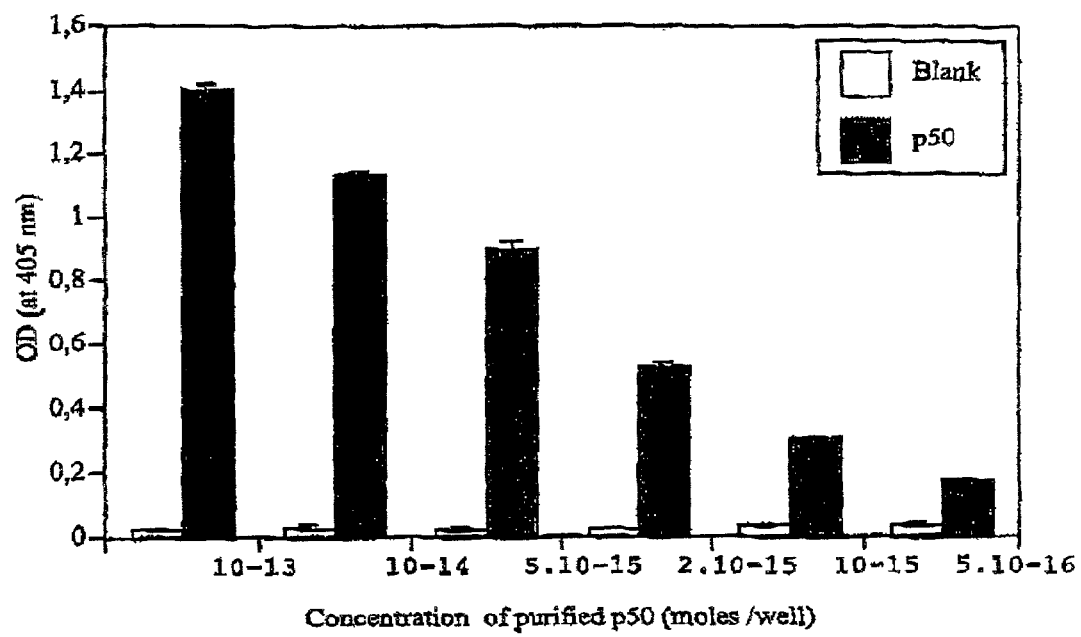

FIG. 3 presents the sensitivity of the DNA-binding assay. DNA-binding activity of purified NFκB (p50) was measured on microwells containing DNA probe specific for NFκB. The concentrations of p50 used in this assay range from $10^{-12}$ mole to $5 \cdot 10^{-16}$ mole/well.

Figure 4:
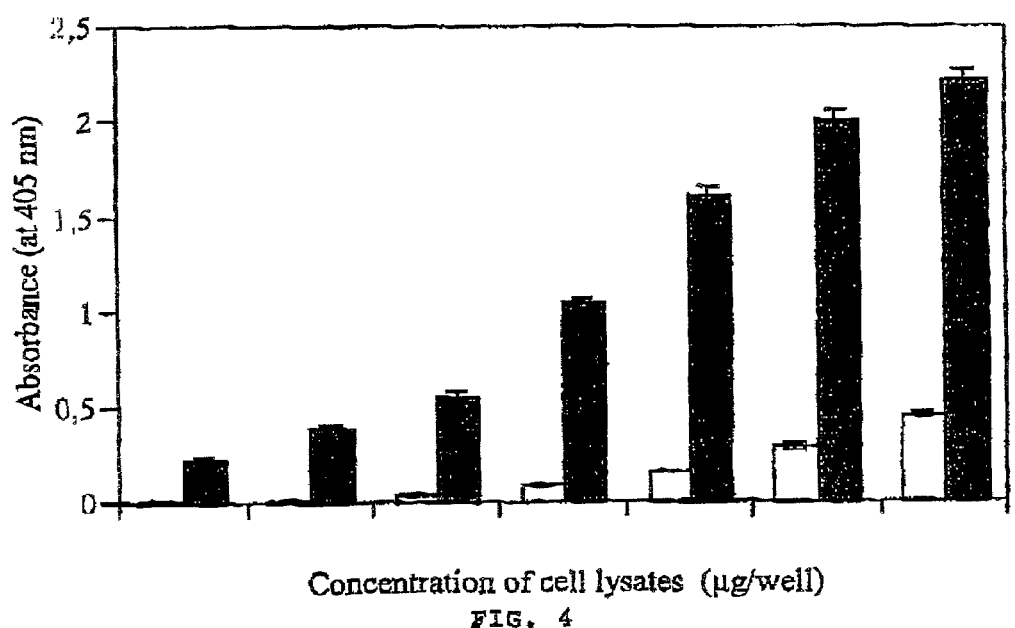

FIG. 4 presents the sensitivity of the DNA binding assay. DNA-binding activity of stimulated cells and unstimulated cells for NFκB.

Figure 5:
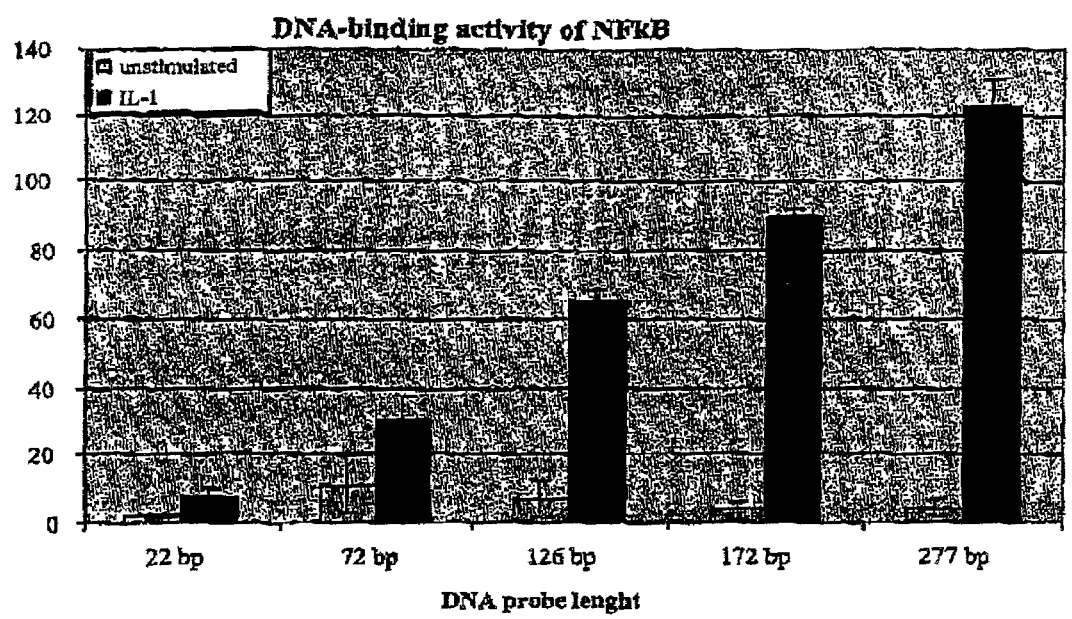

FIG. 5 presents the values obtained for the detection of NKκB present in cells stimulated or not with IL-1 on microarray by using DNA probes of different lengths containing a spotted consensus sequence for NFκB.

Figure 6:
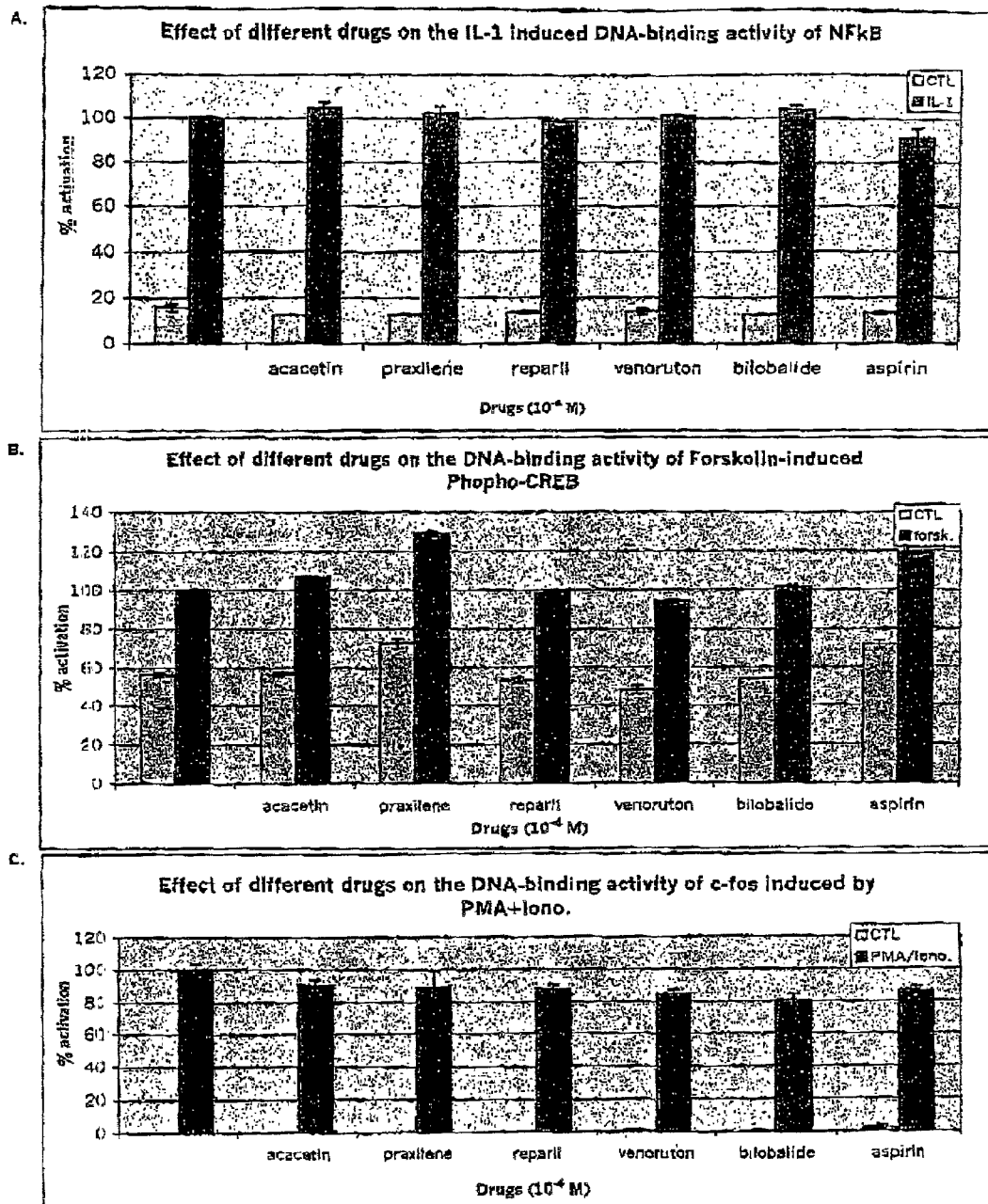

FIG. 6 presents the effect of various drugs on the DNA-binding activity of IL-1-induced NFκB.

EXAMPLES

Example 1

Microwell Colorimetric DNA-binding Assay (FIGS. 1 and 2)

Step 1: Binding of the Double Strand Oligonucleotidic Probe on Multi-well Plates The spacer double strand nucleotide sequences were constructed from the following CMV sequence:
5'TGGCCAAGCGGCCTCTGATAACCAAGC-CTGAGGTTATCAGTGTAATGAAGCGCCG CATGAGGAGATCTGCATGAAGGTCTTTGC-CCAGTACATTCTGGGGGCCGATCCTCT GAGAGTCTGCTCTCCTAGTGTGGATGAC-CTACGGGCCATCGCCGAGGAGTCAGATG AGGAA-GAGGCTATTGTAGCCTACACTTTGGC-CACCGCTGGTGTCAGCTCCTCTGATT CTCTGGTGTCACCCCCAGAGTCCCCTGTAC (SEQ ID NO:146) acting as a spacer was linked to a) the NFκB consensus oligonucleotide 5'AGTTGAGGGGACTTTC-CCAGGC-3' (SEQ ID NO:147) b) the CREB consensus oligonucleotide 5'ATTGCCTGACGTCAGAGAGCTAG-3' (SEQ ID NO:148) and c) the AP-1 consensus oligonucleotide 5'CCGTTCCGGCTGACTCATCAAGCG-3' (SEQ ID NO:149). In the example the spacer was of 100 based pairs. The CMV extremity is 5' biotinylated, so that these probes can be linked to streptavidin-coated 96-wells plates : 2 pmoles of probes per well are incubated 1h at 37° C. in 50 µl 10 mM phosphate buffer 150 mM NaCl (hereafter called $PBS_{150}$). Plates are then washed and the amount of DNA fixed on streptavidin-coated plates was quantified using the picogreen assay (Molecular Probes, OR, USA). One picomole of DNA was found to be fixed on the wells using DNA standard for calibration of the assay.

Step 2: Binding of the Transcription Factor on the Double Strand Probe

This assay was either performed with purified p50-p50 (Promega, Madison, Wis., USA), or with nuclear cell extracts from SV-40 transformed WI-38 fibroblasts (WI-38 VA13 cell line). Cells were purchased from the ATCC and plated in 75 $cm^2$ flasks. They were serially cultivated in Minimum Essential Medium (Gibco, UK) supplemented with $Na_2SeO_3$ $10^{-7}$ M and antibiotics, in the presence of 10% fetal bovine serum. Cells were stimulated for 30 min with IL-1 (to activate NFκB), forskolin (to activate CREB), PMA+ionomycin (to activate AP-1) or left unstimulated.

The nuclear cell extracts were prepared as followed
  cells were rinsed with cold $PBS_{150}$
  cells were left swollen during 3 min in a cold hypotonic buffer (20 mM Hepes pH 7.4, 5 mM NaF, 1 mM $Na_2MoO_4$, 0.1 mM EDTA).
  Cells were scrapped in 0.5 ml of hypotonic buffer containing 0.2% nonidet P40 and immediately centrifuged during 30 sec at maximal speed (13000 rpm).
  The pellet was resuspended in 100 μl of lysis buffer (hypotonic buffer containing 20% glycerol, 0.4 M NaCl, phosphatases and proteases inhibitors cocktail).
  The nuclear extract was agitated 30 min at 4° C., and then centrifuged for 10 min at maximal speed (13000 rpm) at 4° C.
  The supernatant (=nuclear extract) was frozen at –80° C. and its proteic content was determined by the Bradford assay.
  20 μl of p50 diluted in lysis buffer or 20 μl of nuclear cell extract are incubated with 30 μl of binding buffer (AAT, Namur) in microwells coated either with the consensus oligonucleotide for NFκB, or with the consensus oligonucleotide for CREB, or with the consensus oligonucleotide for AP-1. After 2h incubation at room temperature with a mild agitation (200 rpm on IKA MS2 vortex, Germany), microwells are washed 3 times with $PBS_{150}$. with 10 mM phosphate buffer 50 mM NaCl (hereafter called $PBS_{50}$)+Tween 0.1%, and once with $PBS_{50}$ alone.

Step 3: Binding of Anti-NFκB on the NFκB-DNA Complex
  100 μL of rabbit antibodies diluted 500 or 1000 times in 10 mM phosphate buffer 50 mM NaCl (hereafter called $PBS_{50}$) and 1% bovine serum albumine are incubated in each well for 1 h at room temperature. The different antibodies used are:
    for NFκB: anti p65 (Santa Cruz #sc-372) or anti p50 (Santa Cruz #sc-7178)
    for CREB: anti CREB (Rockland, #100-401-195) or anti phospho-CREB (Upstate Biotechnology 06-519).
    for AP-1: anti c-fos (Santa Cruz, #sc-7202) or anti c-jun (Biolabs #9164).
  The microwells are then washed 3 times with $PBS_{150+0.1}$% Tween.

Step 4: Binding of Peroxidase-conjugated Anti-rabbit IgG
  100 μL of diluted peroxidase-conjugated anti-rabbit IgG (#611-1302, Rockland, Gilbertsville, Pa., USA) diluted 1000 times in $PBS_{50}$ and 1% non fat dried milk are incubated in each well for 1 h at room temperature. Microwells are then washed with 200 μl $PBS_{50}$+0.1% Tween.

Step 5: Colorimetric Revelation
  100 μl of tetramethylbenzidine (Biosource, Belgium) are incubated 10 min at room temperature before adding 100 μl of stopping solution (Biosource, Belgium) Optical density is then read at 450 or 405 nm, with an Ultramark microplate reader (Biorad, Calif., USA).
  This procedure can be followed to quantitate the DNA-binding activity of different transcription factors in the same nuclear extract. In FIG. 2, the DNA binding activity of NFκB (a), CREB (b) and AP-1 (c) has been measured on the same samples following the procedure described here above. The samples are nuclear extracts of WI-38 VA13 cells left unstimulated or stimulated during 30 min with 5 ng/ml of IL-1 (a NFκB activator), 10 μg/ml of forskolin (a CREB activator), 0.1 μg/ml PMA+1 μM ionomycin (a cocktail known to activate AP-1), or the different combinations of these activators. The results are expressed as the percentage of the signal obtained with the regular activator the transcription factor assayed (for example, the NFκB DNA-binding activity is expressed as the percentage of the NFκB DNA-binding activity measured in cells stimulated with IL-1 alone).

The results clearly show that the calorimetric DNA-binding assay allows to measure simultaneously the DNA-binding activity of several transcription factors in the same biological sample.

Example 2

Sensitivity of the DNA-binding Calorimetric Assay in Multiwells (FIGS. 3 and 4)

To estimate the sensitivity of the calorimetric DNA-binding assay described in example 1, the assay was performed with the NFκB specific probe first on various quantities of purified p50 (FIG. 3) and then on different quantities of nuclear cell lysates (FIG. 4).

Different quantities of purified p50 ranging from $10^{-13}$ M to $5.10^{-16}$ M were incubated in the microwells containing the NFκB specific probe, and the assay was realised as described in example 1, using anti-p50 antibody. The results presented in FIG. 3 clearly show that this assay is extremely sensitive as the DNA-binding activity of as low as 5.10-16 mole/well of purified p50 can be detected.

The sensitivity of the calorimetric DNA-binding assay with cell lysates is also very high, as shown in FIG. 3. Cell extracts are coming either from unstimulated cells or from cells stimulated with IL-1 in order to proceed for the assay as described in the example 1. In this experiment the concentrations ranged between 0.5 and 50 μg per well. The assay was performed in parallel with EMSA, on the same protein extracts. The results presented on FIG. 4 clearly show that the NFκB DNA-binding assay in microwells is more than 10 times more sensitive than the EMSA: 5 μg of proteins were required to detect a first detection signal by EMSA, but less than 0.5 μg of proteins was necessary for the microwell assay.

Example 3

Microarray Assay for DNA-binding Activity of NF-KB CREB in Biological Samples

Step 1: Binding of the Probes on Glass
  Activated glass slides bearing aldehyde groups were purchased from AAT (Belgium).
  The slides were first incubated in 0.8 ml of a 50 μg/ml streptavidin solution in a 10 mM phosphate buffer (pH 7.4) containing 10 mM NaCl ($PBS_{10}$ buffer). After 1 h incubation at 20° C., the plates were washed 3 times for 2 min in $PBS_{150}$ containing 0.02% Tween 20 and then 2 times 2 min with water. The plates were then incubated for 2 h at 20° C. in 20 ml of $PBS_{150}$ solution containing 10% non fat dried milk and then washed 5 times 2 min in $PBS_{150}$ solution.
  Spotting was performed with the NFκB consensus probe or with the CREB consensus probe as in example 1. The capture probes were printed onto the microscopic slides with a home made robotic device. 250 μm pins from Genetix (UK) were used. The spots have an average of 400 μm in diameter and the volume dispensed is about 1 nl. The concentration of probes used was 3000 nmolaire. Slides were incubated for 1 h at room temperature, washed twice for 2 min with $PBS_{50}$ containing 0.02% Tween 20 and then 3 times for 2 min in water.

Step 2: Binding of Transcription Factor on the Double Strand Probe Fixed on Micro-array This assay was performed with nuclear extracts from WI-38 VA 13 fibroblasts stimulated with IL-1β or left unstimulated. The cell extracts were prepared as described in the example 1. The negative control was 20 μl of lysis buffer mixed with 30 μl of binding buffer. 20 μl of p50 diluted in lysis buffer or 20 μl of nuclear cell extract are incubated with 30 μl of binding buffer (AAT, Namur, Belgium) per incubation chamber. After 1 h incubation at room temperature with a mild agitation (200 rpm on IKA MS2 vortex, Germany), the arrays were washed 3 times.

Steps 3, 4 and 5: Binding of Anti-NFκB on the NFκB-DNA Complex and Detection

The binding of the primary anti-NFκB (anti-p50) antibody was then used for reaction on the factor followed by a washing and an incubation with a secondary antibody. In this case, the second antibody was gold-labelled. After 3 incubations of 10 min in a mixture of silver enhancer A, the slides were washed with water.

There was no signal for the negative control, while in nuclear cell extracts, activated NFκB is detectable in cell stimulated with IL-1, with a much higher intensity than in unstimulated. The results obtained with the nuclear cell extracts have been quantitated, using a calorimetric microarray reader including the quantification software (AAT, Namur, Belgium). The intensity of each spot was estimated by averaging the value of all pixels inside its boundaries. The value of the mean background around the spot was subtracted from the spot values. The value for the unstimulated cells was of 10 and the one for the stimulated cell were of 175 grey intensity.

As an alternative fixation of the probes, the consensus sequences were aminated by using a 5'terminal aminated primer and amplified by PCR before being spotted directly on the aldehyde glass slides. The detection method was then processed in the same way as here above.

Example 4

Influence of the Spacer on Microarray Assay of of NFκB and CREB Assay on Biological Samples (FIG. 5)

Step 1: Binding of the Probes on Glass.

The binding of probes was obtained as described in the example 3 using the consensus sequence of NF-KB or CREB alone or with a spacer of 50, 100, 150 and 250 bp constructed from the sequence given in example 1.

Step 2: Binding of NFκB on the Double Strand Probe Fixed on Micro-array

This assay was performed with whole cell lysates from WI-38 VA 13 fibroblasts stimulated with IL-1β (a NFκB activator) or 10 μg/ml of forskolin(to activate CREB). The control was 20 μl of lysis buffer mixed with 30 μl of binding buffer.

Steps 3, 4 and 5: Binding of Antibodies and Detection

The binding of the primary anti-NFκB and anti-PCREB antibodies was then used for reaction on the factors followed by a second gold labelled antibody and a calorimetric detection as in example 3. The results with increasing spacer length for the NF-KB is shown in FIG. 5. The figure shows the total length of the fixed DNA probes. The values for P-CREB with unstimulated cells were 5.5 and 4 respectively with no spacer and with a 100 base spacer. The values for stimulated cells were respectively of 7 and 21 respectively with no spacer and a spacer of 100 bases pairs.

Example 5

Use of the DNA-binding Calorimetric Assay to Screen for DNA-binding Interacting Drugs (FIG. 6)

The DNA-binding colorimetric assay was used for screening of molecules, like drugs, that can interfere either directly with the DNA-binding capacity of a transcription factor or with the upstream cellular activation process of a transcription factor.

In FIG. 6, several molecules known as drugs were screened for their eventual inhibitory effect on the DNA-binding capacity of 3 transcription factors. 5 μg of nuclear extracts prepared as in example 1 from a) IL-1-stimulated fibroblasts or b)Forskolin-stimulated cells or c) PMA+ionomycin-stimulated cells were assayed respectively for the DNA-binding capacity of NFκB, CREB an AP-1, in the presence of absence of various veinotropic drugs at $10^{-4}M$.

The molecules were tested on the activation of the factors in the following way. Cells were incubated in the presence of the molecules at a concentration of $10^{-5}M$ for one hour before the stimulation with IL-1, Forskolin or PMA+ionomycin. Nuclear extracts were prepared and the activity of the transcriptional factors measured as described in example 1.

TABLE 1

List of transcriptional factors and their consensus sequences

| | | |
|---|---|---|
| AAF | TTTCATATTACTCT | (SEQ ID NO:1) |
| AbdB | AA(A/T)TTTTATTAC | (SEQ ID NO:2) |
| AhR | TGCGTGAGAAGA | (SEQ ID NO:3) |
| Antp | AA(A/T)TTTAATTAC | (SEQ ID NO:4) |

TABLE 1-continued

List of transcriptional factors and their consensus sequences

| | | |
|---|---|---|
| Ap1 | TGASTMA | (SEQ ID NO:5) |
| AP2 | CCCMCNSSS | (SEQ ID NO:6) |
| AP3 | TGTGGWWW | (SEQ ID NO:7) |
| AP4 | YCAGCTGYGG | (SEQ ID NO:8) |
| AR | AGAACANNNTGTTCT | (SEQ ID NO:9) |
| ARNt | GTG (3'-half site) | (SEQ ID NO:10) |
| ARP-1 | TGANCCCTTGACCCCT | (SEQ ID NO:11) |
| ATF | TGACGYMR | (SEQ ID NO:12) |
| BGP1 | GGGGGGGGGGGGGGG | (SEQ ID NO:13) |
| BSAP | GACGCANYGRWNNNMG | (SEQ ID NO:14) |
| CBF | ACACCCAAATATGGCGAC | (SEQ ID NO:15) |
| C/EBP | GTGGWWWC | (SEQ ID NO:16) |
| CF1 | ANATGG | (SEQ ID NO:17) |
| COUP | GTGTCAAAGCTCA | (SEQ ID NO:18) |
| CP1 | YNNNNNNNRRCCAATCANYK | (SEQ ID NO:19) |
| CP2 | YAGYNNNRRCCAATCNNNR | (SEQ ID NO:20) |
| CTCF | CCCTC | (SEQ ID NO:21) |
| DBP | TGATTTTGT | (SEQ ID NO:22) |
| E2A | RCAGNTG | (SEQ ID NO:23) |
| E2B | TGCAAYAY | (SEQ ID NO:24) |
| E2F | TTTTSSCGS | (SEQ ID NO:25) |
| E4F | TGACGTAAC | (SEQ ID NO:26) |
| EGR-1 | CGCCCSCGC | (SEQ ID NO:27) |
| EGR-2 | CCGCCCCCGC | (SEQ ID NO:28) |
| ER | AGGTCANNNTGACCT | (SEQ ID NO:29) |
| v-ErbA | GTGTCAAAGGTCA | (SEQ ID NO:30) |
| ETF | CAGCCCCCGCGCAGC | (SEQ ID NO:31) |
| Ets-1 | SMGGAWGY | (SEQ ID NO:32) |
| F-ACT1 | TGGCGA | (SEQ ID NO:33) |
| GAL 4 | CGGN$_5$(T/A)N$_5$CCG | (SEQ ID NO:34) |
| GATA-1 | WGATAR | (SEQ ID NO:35) |
| GATA-2 | WGATAR | (SEQ ID NO:36) |
| GATA-3 | WGATAR | (SEQ ID NO:37) |
| GCF | SCGSSSC | (SEQ ID NO:38) |
| GHF-1 | WTATYCAT | (SEQ ID NO:39) |
| GHF-5 | WTATYCAT | (SEQ ID NO:40) |
| GHF-7 | WTATYCAT | (SEQ ID NO:41) |
| GR | AGAACANNNTGTTCT | (SEQ ID NO:42) |

TABLE 1-continued

List of transcriptional factors and their consensus sequences

| | | |
|---|---|---|
| H1TF2 | GCACCAATCACAGCGCGC | (SEQ ID NO:43) |
| H2RIIBP | TCAGGTCACAGTGACCTGA | (SEQ ID NO:44) |
| H2TF1 | TGGGGATTCCCCA | (SEQ ID NO:45) |
| H-APF-1 | CTGGRAA | (SEQ ID NO:46) |
| HIF | CTACGTGCT | (SEQ ID NO:47) |
| HNF-1 | GTTAATNATTAAC | (SEQ ID NO:48) |
| vHNF-1 | GTTAATNATTAAC | (SEQ ID NO:49) |
| HNF-3A | TATTGAYTTWG | (SEQ ID NO:50) |
| HNF-3B | TATTGAYTTWG | (SEQ ID NO:51) |
| HNF-3C | TATTGAYTTWG | (SEQ ID NO:52) |
| HNF-4 | KGCWARGKYCAY | (SEQ ID NO:53) |
| HSF | NGAANNGAANNGAAN | (SEQ ID NO:54) |
| IAF | GCCATCTGCT | (SEQ ID NO:55) |
| IRBP | AGTGCACT | (SEQ ID NO:56) |
| IREBF-1 | CGGGAAATGGAAACTG | (SEQ ID ND:57) |
| IRF | AANNGA | (SEQ ID NO:58) |
| ISGF1 | CTTTCAGTTT | (SEQ ID NO:59) |
| ISGF2 | CTTTCTCTTT | (SEQ ID NO:60) |
| ISGF3 | GCTTCAGTTT | (SEQ ID NO:61) |
| KBF-1 | TGGGGATTCCCCA | (SEQ ID NO:62) |
| Ker1 | GCCTGCAGGC | (SEQ ID NO:63) |
| LFB3 | GTTAATNATTAAC | (SEQ ID NO:64) |
| LIT-1 | GCGCCCTTTGGACCT | (SEQ ID NO:65) |
| LyF-1 | YYTGGGAGR | (SEQ ID NO:66) |
| MBF-1 | YTAAAAATAAYYY | (SEQ ID NO:67) |
| MBF-I | TGCRCRC | (SEQ ID NO:68) |
| MBP-1 | TGGGGATTCCCCA | (SEQ ID NO:69) |
| MCBF | CATTCCT | (SEQ ID NO:70) |
| MEF-2 | YTAWAAATAR | (SEQ ID NO:71) |
| MEP-1 | TGCRCNC | (SEQ ID NO:72) |
| MR | AGAACANNNTGTTCT | (SEQ ID NO:73) |
| Myb | YAACKG | (SEQ ID NO:74) |
| Myc | CACGTG | (SEQ ID NO:75) |
| Myc | TCTCTTA | (SEQ ID NO:150) |
| MyoD | CAACTGAC | (SEQ ID NO:76) |
| NF1 | YGGMNNNNNGCCAA | (SEQ ID NO:77) |
| NF-AT | GGAGGAAAAACTGTTTCAT | (SEQ ID NO:78) |
| NF-E2 | TGACTCAG | (SEQ ID NO:79) |

TABLE 1-continued

List of transcriptional factors and their consensus sequences

| | | |
|---|---|---|
| NF-D | GATGGCGG | (SEQ ID NO:80) |
| NF-GMa | GRGRGTTKCAY | (SEQ ID NO:81) |
| NF-GMb | TCAGRTA | (SEQ ID NO:82) |
| NF-IL6 | TKNNGNAAK | (SEQ ID NO:83) |
| NFxB | GGGAMTNYCC | (SEQ ID NO:84) |
| NF-W1 | GTTGCATC | (SEQ ID NO:85) |
| NF-W2 | GTTGCATC | (SEQ ID NO:86) |
| NGF1-B | AGGTCATGACCT | (SEQ ID NO:87) |
| Oct-1 | ATGCAAAT | (SEQ ID NO:88) |
| Oct-2 | ATGCAAAT | (SEQ ID NO:89) |
| Oct-4 | ATGCWAAT | (SEQ ID NO:90) |
| Oct-6 | ATGCAAAT | (SEQ ID NO:91) |
| P53 | RRRC(A/T)(T/A)GYYY(N)$_{0-13}$RRRC(A/T)(T/A)GYYY | (SEQ ID NO:92); (SEQ ID NO:133-SEQ ID NO:145) |
| Pax-1 | CACCGTTCCGCTCTAGATATCTC | (SEQ ID NO:93) |
| PCF | AGAAAGGGAAAGGA | (SEQ ID NO:94) |
| PEA3 | AGGAAR | (SEQ ID NO:95) |
| PPAR | AGGTCA | (SEQ ID NO:96) |
| PR | AGAACANNNTGTTCT | (SEQ ID NO:97) |
| PRDI-BF1 | AAGTGAAAGT | (SEQ ID NO:98) |
| PTF1 | ATGGGANCTCAGCTGTGC | (SEQ ID NO:99) |
| Pu.I | AGAGGAACT | (SEQ ID NO:100) |
| PuF | GGGTGGG | (SEQ ID NO:101) |
| RAR | AGGTCATGACCT | (SEQ ID NO:102) |
| RFX | CCCCTAGCAACAGATG | (SEQ ID NO:103) |
| Runt | YGYGGT | (SEQ ID NO:104) |
| RVF | AAGATAAAACC | (SEQ ID NO:105) |
| RXR | AGGTCA (in a Direct Repeat configuration) | (SEQ ID NO:106) |
| SIF | CCCGTM | (SEQ ID NO:107) |
| Sp1 | KRGGCTRRK | (SEQ ID NO:108) |
| SREBP1 | ATCACGTGA (E-Box consensus binding sequence) | (SEQ ID NO:109) |
| | or ATCACCCCAC (non E-Box consensus bindingsequence) | (SEQ ID NO:110) |
| SRF | GGATGTCCATATTAGGACATCT | (SEQ ID NO:111) |
| STAT | TTCNNNGAA | (SEQ ID NO:112) |
| T3R | AGGTCATGACCT | (SEQ ID NO:113) |
| TBP | TATAAA | (SEQ ID NO:114) |
| TCF-1 | MAMAG | (SEQ ID NO:115) |

TABLE 1-continued

List of transcriptional factors and their consensus sequences

| | | |
|---|---|---|
| TCF-2.alpha. | SAGGAAGY | (SEQ ID NO:116) |
| TEF-1 | AAGYATGCA | (SEQ ID NO:117) |
| TEF-2 | GGGTGTGG | (SEQ ID NO:118) |
| TGT3 | AAGTGTTTGC | (SEQ ID NO:119) |
| TIN-1 | AGGAAGTTCC | (SEQ ID NO:120) |
| USF | CACGTG | (SEQ ID NO:121) |
| WT-ZFP | CGCCCCGC | (SEQ ID NO:122) |
| XF1/2 | TCTTCTCACGCAACT | (SEQ ID NO:123) |
| XPF-1 | CACCTGNNNNTTTCCC | (SEQ ID NO:124) |
| YB-1 | ATTTTTCTGATTGGCCAAAG | (SEQ ID NO:125) |

List of viral proteins binding to DNA

| | | |
|---|---|---|
| Epstein-Barr Virus EBNA (B958 strain) | GGT TAG CAT ATG CTA ACC A (SEQ ID NO:127) | (SEQ ID NO:126) |
| Epstein-Barr Virus BZLF | T TAG CAA TG | (SEQ ID NO:127) (B958 strain) |
| Human CBF-1 | CGTGGGAA (EpsteinBarr Virus cis-element) | (SEQ ID NO:128) |
| Human Papilloma | A CCG AAA ACG GTG T | (SEQ ID NO:129) |
| Herpes Simplex Virus Type 1 | ATG CTA ATG ATA VP16 | (SEQ ID NO:130) |
| HIV TAT | GGG TCT CTC TGG TTA GAC CAG ATC TGA GCC TGG GAG CTC TCT GGC TAA CTA GGG AAC CCA (TAR RNA SEQUENCE) | (SEQ ID NO:131) |
| HIV Integrase | GTGTGGAAAATCTCTAGCA | (SEQ ID NO:132) |

Abreviations: R = (A,g) - Y = (C,T) - M = (A,C) - K = (g,T) - S = (g,C) - H = (A,T,C) - B = (g,T,C) - D = (g,A,T) - N = (A,g,C,T) - V = (g,A,C) - X = (C,I) - W = (A,T) - 0 = Sme-dC - Q = 5Br-dU - I = Inosine

---

What is claimed is:

1. A screening and/or quantification method of one or more activated transcriptional factors(s) present in a cell or cell lysate, said method comprising the steps of:
   (a) binding to an insoluble solid support double-stranded DNA sequence(s) at the concentration of at least 0.01 pmole/cm$^2$ of said solid support surface, wherein the solid support is an array bearing at least 4 spots/cm$^2$ of solid support surface, each spot containing double-stranded DNA sequence(s) for the binding of activated transcriptional factor(s), said double-stranded DNA sequence comprising a specific sequence, said specific sequence being able to bind said one or more activated transcriptional factor(s) and said double-stranded DNA sequence being connected to the surface of the solid support by a spacer wherein said spacer is a double-stranded DNA nucleotide sequence of between about 50 and about 250 base pairs, or wherein the spacer comprises a double-stranded DNA nucleotide sequence of between about 50 and about 250 base pairs, and wherein said double-stranded DNA nucleotide sequence of between about 50 and about 250 base pairs is not present in said cell;
   (b) putting into contact said one or more activated transcriptional factor(s) with said bound double-stranded DNA sequence(s); and
   (c) identifying and/or quantifying a signal specific for the binding of said activated transcriptional factor(s) upon said double-stranded DNA sequence(s).

2. The method according to claim 1, wherein the transcriptional factor is present in solution at concentration lower than 20 nmolar (nM).

3. The method according to claim 1, wherein the signal resulting from the binding of the activated transcriptional factor upon the double-stranded DNA sequence is a non-radioactive signal.

4. The method according to claim 1, wherein the signal resulting from the binding of the activated transcriptional factor upon the double-stranded DNA sequence is obtained through an enzymatic reaction.

5. The method according to claim 1, wherein said activated transcriptional factors are present in same biological sample.

6. The method according to claim 1, wherein said activated transcriptional factors are selected from the group consisting of NF-KB, AP-1, CREB, SP-1, C/EBP, GR, HIF-1, Myc, NF-AT, Oct, TBP, CBF-1 and factors listed in table 1.

7. The method according to claim 1, wherein said one or more activated transcriptional factors are put into contact with said bound double-stranded DNA sequence(s) upon same support or upon same multiwell plate.

8. The method according to claim 1, wherein the binding of the double-stranded DNA sequence(s) to the solid support is of non-covalent type and includes a binding pair comprising a first member and a second member, said first member being bound to the double-stranded DNA sequence, said second member being bound to the surface of the solid support.

9. The method of claim 8, wherein said binding pair is biotin/streptavidin.

10. The method according to claim 8, wherein the binding pair is selected from the group consisting of biotin/streptavidin, hapten/receptor and antigen/antibody binding pair.

11. The method according to claim 1, wherein the double-stranded DNA sequence(s) are covalently bound to the surface of the insoluble solid support.

12. The method according to claim 1, wherein the double-stranded DNA sequence comprises repeated specific sequences.

13. The method according to claim 1, wherein the double-stranded DNA sequences fixed on the support surface contain one or several of the specific DNA sequences presented in the table 1.

14. The method according to claim 1, comprising the step of identifying at least one characteristic specific of the transcriptional factor activation.

15. The method according to claim 1, which comprises the steps of screening, quantifying and/or recovering compounds able to bind to said activated transcriptional factor(s) or inhibit the binding of said activated transcriptional factor(s) to the specific sequence upon the double-stranded DNA sequence(s) bound to said solid support.

16. The method according to claim 1, which further comprises prior to step (b) the step of contacting said cells with a candidate compound which is being evaluated to determine whether it modulates the binding and/or activity of the said activated transcriptional factor(s).

17. The method according to claim 1, wherein step (c) comprises the step of identifying activated transcriptional factor(s) and/or peptides which are part of the activated transcriptional factor(s) complex.

18. The method according to claim 1, which comprises the step of adding in the cell lysate an externally added transcriptional factor or a compound which is able to bind to the specific sequence.

19. The method according to claim 1, wherein step b) comprises putting into contact said one or more activated transcriptional factor(s) in a cell lysate with said bound double-stranded DNA sequence(s).

20. The method of claim 1, wherein said identifying and/or quantifying said signal is obtained, detected and/or quantified by addition of antibodies specific for the activated transcriptional factor(s).

21. The method of claim 1, wherein said identifying and/or quantifying said signal is obtained, detected and/or quantified by addition of antibodies specific for compounds involved in the formation of an activation complex comprising said transcriptional factors.

22. A screening and/or quantification method of one or more activated transcriptional factors(s) present in a cell or cell lysate, said method comprising the steps of:
   (a) binding to an insoluble solid support double-stranded DNA sequence(s) at the concentration of at least 0.01 pmole/cm$^2$ of said solid support surface, wherein the solid support is an array bearing at least 4 spots/cm$^2$ of solid support surface, each spot containing double-stranded DNA sequence(s) for the binding of activated transcriptional factor(s), said double-stranded DNA sequence comprising a specific sequence, said specific sequence being able to bind said one or more activated transcriptional factor(s) and said double-stranded DNA sequence being connected to the surface of the solid support by a spacer wherein said spacer is a double-stranded DNA nucleotide sequence of between about 50 and about 250 base pairs, or wherein the spacer comprises a double-stranded DNA nucleotide sequence of between about 50 and about 250 base pairs, and wherein said double-stranded DNA nucleotide sequence of between about 50 and about 250 base pairs is not present in said cell;

(b) putting into contact said one or more activated transcriptional factor(s) with said bound double-stranded DNA sequence(s); and (c) identifying and/or quantifying a signal specific for the binding of said activated transcriptional factor(s) upon said double-stranded DNA sequence(s), wherein said activated transcriptional factor is the HIV integrase.

* * * * *

SEQUENCE LISTING

<160> NUMBER OF SEQ ID NOS: 150

<210> SEQ ID NO 1
<211> LENGTH: 14
<212> TYPE: DNA
<213> ORGANISM: Artificial Sequence
<220> FEATURE:
<223> OTHER INFORMATION: Consensus sequence for transcriptional factor
      AAF

<400> SEQUENCE: 1
tttcatatta ctct                                                    14

<210> SEQ ID NO 2
<211> LENGTH: 13
<212> TYPE: DNA

-continued

```
<213> ORGANISM: Artificial Sequence
<220> FEATURE:
<223> OTHER INFORMATION: Consensus sequence for transcriptional factor
      AbdB

<400> SEQUENCE: 2
aawtttttat tac                                                    13

<210> SEQ ID NO 3
<211> LENGTH: 12
<212> TYPE: DNA
<213> ORGANISM: Artificial Sequence
<220> FEATURE:
<223> OTHER INFORMATION: Consensus sequence for transcriptional factor
      AhR

<400> SEQUENCE: 3
tgcgtgagaa ga                                                     12

<210> SEQ ID NO 4
<211> LENGTH: 13
<212> TYPE: DNA
<213> ORGANISM: Artificial Sequence
<220> FEATURE:
<223> OTHER INFORMATION: Consensus sequence for transcriptional factor
      Antp

<400> SEQUENCE: 4
aawttttaat tac                                                    13

<210> SEQ ID NO 5
<211> LENGTH: 7
<212> TYPE: DNA
<213> ORGANISM: Artificial Sequence
<220> FEATURE:
<223> OTHER INFORMATION: Consensus sequence for transcriptional factor
      Ap1

<400> SEQUENCE: 5 tgastma                                                            7

<210> SEQ ID NO 6
<211> LENGTH: 9
<212> TYPE: DNA
<213> ORGANISM: Artificial Sequence
<220> FEATURE:
<223> OTHER INFORMATION: Consensus sequence for transcriptional factor
      Ap2
<221> NAME/KEY: misc_feature
<222> LOCATION: (1)...(9)
<223> OTHER INFORMATION: n = A,T,C or G

<400> SEQUENCE: 6 cccmcnsss                                                          9

<210> SEQ ID NO 7
<211> LENGTH: 8
<212> TYPE: DNA
<213> ORGANISM: Artificial Sequence
<220> FEATURE:
<223> OTHER INFORMATION: Consensus sequence for transcriptional factor
      AP3

<400> SEQUENCE: 7 tgtggwww                                                           8

<210> SEQ ID NO 8
```

```
<211> LENGTH: 10
<212> TYPE: DNA
<213> ORGANISM: Artificial Sequence
<220> FEATURE:
<223> OTHER INFORMATION: Consensus sequence for transcriptional factor
      AP4

<400> SEQUENCE: 8 ycagctgygg                                                              10

<210> SEQ ID NO 9
<211> LENGTH: 15
<212> TYPE: DNA
<213> ORGANISM: Artificial Sequence
<220> FEATURE:
<223> OTHER INFORMATION: Consensus sequence for transcriptional factor
      AR
<221> NAME/KEY: misc_feature
<222> LOCATION: (1)...(15)
<223> OTHER INFORMATION: n = A,T,C or G

<400> SEQUENCE: 9
agaacannnt gttct                                                        15

<210> SEQ ID NO 10
<211> LENGTH: 3
<212> TYPE: DNA
<213> ORGANISM: Artificial Sequence
<220> FEATURE:
<223> OTHER INFORMATION: Consensus sequence for transcriptional factor
      ARNt
<221> NAME/KEY: misc_difference
<222> LOCATION: (0)...(0)
<223> OTHER INFORMATION: 3'-half site

<400> SEQUENCE: 10 gtg                                                                      3

<210> SEQ ID NO 11
<211> LENGTH: 16
<212> TYPE: DNA
<213> ORGANISM: Artificial Sequence
<220> FEATURE:
<223> OTHER INFORMATION: Consensus sequence for transcriptional factor
      ARP-1
<221> NAME/KEY: misc_feature
<222> LOCATION: (1)...(16)
<223> OTHER INFORMATION: n = A,T,C or G

<400> SEQUENCE: 11
tgancccttg acccct                                                       16

<210> SEQ ID NO 12
<211> LENGTH: 8
<212> TYPE: DNA
<213> ORGANISM: Artificial Sequence
<220> FEATURE:
<223> OTHER INFORMATION: Consensus sequence for transcriptional factor
      ATF

<400> SEQUENCE: 12 tgacgymr                                                                 8

<210> SEQ ID NO 13
<211> LENGTH: 16
<212> TYPE: DNA
<213> ORGANISM: Artificial Sequence
<220> FEATURE:
<223> OTHER INFORMATION: Consensus sequence for transcriptional factor
```

```
        BGP-1

<400> SEQUENCE: 13
gggggggggg gggggg                                                            16

<210> SEQ ID NO 14
<211> LENGTH: 16
<212> TYPE: DNA
<213> ORGANISM: Artificial Sequence
<220> FEATURE:
<223> OTHER INFORMATION: Consensus sequence for transcriptional factor
      BSAP
<221> NAME/KEY: misc_feature
<222> LOCATION: (1)...(16)
<223> OTHER INFORMATION: n = A,T,C or G

<400> SEQUENCE: 14
gacgcanygr wnnnmg                                                            16

<210> SEQ ID NO 15
<211> LENGTH: 18
<212> TYPE: DNA
<213> ORGANISM: Artificial Sequence
<220> FEATURE:
<223> OTHER INFORMATION: Consensus sequence for transcriptional factor
      CBF

<400> SEQUENCE: 15
acacccaaat atggcgac                                                          18

<210> SEQ ID NO 16
<211> LENGTH: 8
<212> TYPE: DNA
<213> ORGANISM: Artificial Sequence
<220> FEATURE:
<223> OTHER INFORMATION: Consensus sequence for transcriptional factor
      C/EBP

<400> SEQUENCE: 16 gtggwwwg                                                                      8

<210> SEQ ID NO 17
<211> LENGTH: 6
<212> TYPE: DNA
<213> ORGANISM: Artificial Sequence
<220> FEATURE:
<223> OTHER INFORMATION: Consensus sequence for transcriptional factor
      CF1
<221> NAME/KEY: misc_feature
<222> LOCATION: (1)...(6)
<223> OTHER INFORMATION: n = A,T,C or G

<400> SEQUENCE: 17 anatgg                                                                        6

<210> SEQ ID NO 18
<211> LENGTH: 13
<212> TYPE: DNA
<213> ORGANISM: Artificial Sequence
<220> FEATURE:
<223> OTHER INFORMATION: Consensus sequence for transcriptional factor
      COUP

<400> SEQUENCE: 18
gtgtcaaagg tca                                                               13

<210> SEQ ID NO 19
```

```
<211> LENGTH: 19
<212> TYPE: DNA
<213> ORGANISM: Artificial Sequence
<220> FEATURE:
<223> OTHER INFORMATION: Consensus sequence for transcriptional factor
      CP1
<221> NAME/KEY: misc_feature
<222> LOCATION: (1)...(19)
<223> OTHER INFORMATION: n = A,T,C or G

<400> SEQUENCE: 19
ynnnnnnrrc caatcanyk                                              19

<210> SEQ ID NO 20
<211> LENGTH: 19
<212> TYPE: DNA
<213> ORGANISM: Artificial Sequence
<220> FEATURE:
<223> OTHER INFORMATION: Consensus sequence for transcriptional factor
      CP2
<221> NAME/KEY: misc_feature
<222> LOCATION: (1)...(19)
<223> OTHER INFORMATION: n = A,T,C or G

<400> SEQUENCE: 20
yagynnnrrc caatcnnnr                                              19

<210> SEQ ID NO 21
<211> LENGTH: 5
<212> TYPE: DNA
<213> ORGANISM: Artificial Sequence
<220> FEATURE:
<223> OTHER INFORMATION: Consensus sequence for transcriptional factor
      CTCF

<400> SEQUENCE: 21 ccctc                                                              5

<210> SEQ ID NO 22
<211> LENGTH: 9
<212> TYPE: DNA
<213> ORGANISM: Artificial Sequence
<220> FEATURE:
<223> OTHER INFORMATION: Consensus sequence for transcriptional factor
      DBP

<400> SEQUENCE: 22 tgattttgt                                                          9

<210> SEQ ID NO 23
<211> LENGTH: 7
<212> TYPE: DNA
<213> ORGANISM: Artificial Sequence
<220> FEATURE:
<223> OTHER INFORMATION: Consensus sequence for transcriptional factor
      E2A
<221> NAME/KEY: misc_feature
<222> LOCATION: (1)...(7)
<223> OTHER INFORMATION: n = A,T,C or G

<400> SEQUENCE: 23 rcagntg                                                            7

<210> SEQ ID NO 24
<211> LENGTH: 8
<212> TYPE: DNA
<213> ORGANISM: Artificial Sequence
<220> FEATURE:
<223> OTHER INFORMATION: Consensus sequence for transcriptional factor
```

```
                              E2B

<400> SEQUENCE: 24 tgcaayay                                                              8

<210> SEQ ID NO 25
<211> LENGTH: 9
<212> TYPE: DNA
<213> ORGANISM: Artificial Sequence
<220> FEATURE:
<223> OTHER INFORMATION: Consensus sequence for transcriptional factor
      E2F

<400> SEQUENCE: 25 ttttsscgs                                                             9

<210> SEQ ID NO 26
<211> LENGTH: 9
<212> TYPE: DNA
<213> ORGANISM: Artificial Sequence
<220> FEATURE:
<223> OTHER INFORMATION: Consensus sequence for transcriptional factor
      E4F

<400> SEQUENCE: 26 tgacgtaac                                                             9

<210> SEQ ID NO 27
<211> LENGTH: 9
<212> TYPE: DNA
<213> ORGANISM: Artificial Sequence
<220> FEATURE:
<223> OTHER INFORMATION: Consensus sequence for transcriptional factor
      EGR-1

<400> SEQUENCE: 27 cgcccscgc                                                             9

<210> SEQ ID NO 28
<211> LENGTH: 10
<212> TYPE: DNA
<213> ORGANISM: Artificial Sequence
<220> FEATURE:
<223> OTHER INFORMATION: Consensus sequence for transcriptional factor
      EGR-2

<400> SEQUENCE: 28
ccgcccccgc                                                           10

<210> SEQ ID NO 29
<211> LENGTH: 15
<212> TYPE: DNA
<213> ORGANISM: Artificial Sequence
<220> FEATURE:
<223> OTHER INFORMATION: Consensus sequence for transcriptional factor
      ER
<221> NAME/KEY: misc_feature
<222> LOCATION: (1)...(15)
<223> OTHER INFORMATION: n = A,T,C or G

<400> SEQUENCE: 29
aggtcannnt gacct                                                     15

<210> SEQ ID NO 30
<211> LENGTH: 13
<212> TYPE: DNA
<213> ORGANISM: Artificial Sequence
```

```
<220> FEATURE:
<223> OTHER INFORMATION: Consensus sequence for transcriptional factor
      v-ErbA

<400> SEQUENCE: 30
gtgtcaaagg tca                                                          13

<210> SEQ ID NO 31
<211> LENGTH: 15
<212> TYPE: DNA
<213> ORGANISM: Artificial Sequence
<220> FEATURE:
<223> OTHER INFORMATION: Consensus sequence for transcriptional factor
      ETF

<400> SEQUENCE: 31
cagcccccgc gcagc                                                        15

<210> SEQ ID NO 32
<211> LENGTH: 8
<212> TYPE: DNA
<213> ORGANISM: Artificial Sequence
<220> FEATURE:
<223> OTHER INFORMATION: Consensus sequence for transcriptional factor
      Ets-1

<400> SEQUENCE: 32 smggawgy                                                                 8

<210> SEQ ID NO 33
<211> LENGTH: 6
<212> TYPE: DNA
<213> ORGANISM: Artificial Sequence
<220> FEATURE:
<223> OTHER INFORMATION: Consensus sequence for transcriptional factor
      F-ACT1

<400> SEQUENCE: 33 tggcga                                                                   6

<210> SEQ ID NO 34
<211> LENGTH: 17
<212> TYPE: DNA
<213> ORGANISM: Artificial Sequence
<220> FEATURE:
<223> OTHER INFORMATION: Consensus sequence for transcriptional factor
      GAL4
<221> NAME/KEY: misc_feature
<222> LOCATION: (1)...(17)
<223> OTHER INFORMATION: n = A,T,C or G

<400> SEQUENCE: 34
cggnnnnnwn nnnnccg                                                      17

<210> SEQ ID NO 35
<211> LENGTH: 6
<212> TYPE: DNA
<213> ORGANISM: Artificial Sequence
<220> FEATURE:
<223> OTHER INFORMATION: Consensus sequence for transcriptional factor
      GATA-1

<400> SEQUENCE: 35 wgatar                                                                   6

<210> SEQ ID NO 36
<211> LENGTH: 6
```

```
<212> TYPE: DNA
<213> ORGANISM: Artificial Sequence
<220> FEATURE:
<223> OTHER INFORMATION: Consensus sequence for transcriptional factor
      GATA-2

<400> SEQUENCE: 36 wgatar                                                                    6

<210> SEQ ID NO 37
<211> LENGTH: 6
<212> TYPE: DNA
<213> ORGANISM: Artificial Sequence
<220> FEATURE:
<223> OTHER INFORMATION: Consensus sequence for transcriptional factor
      GATA-3

<400> SEQUENCE: 37 wgatar                                                                    6

<210> SEQ ID NO 38
<211> LENGTH: 7
<212> TYPE: DNA
<213> ORGANISM: Artificial Sequence
<220> FEATURE:
<223> OTHER INFORMATION: Consensus sequence for transcriptional factor
      GCF

<400> SEQUENCE: 38 scgsssc                                                                   7

<210> SEQ ID NO 39
<211> LENGTH: 8
<212> TYPE: DNA
<213> ORGANISM: Artificial Sequence
<220> FEATURE:
<223> OTHER INFORMATION: Consensus sequence for transcriptional factor
      GHF-1

<400> SEQUENCE: 39 wtatycat                                                                  8

<210> SEQ ID NO 40
<211> LENGTH: 8
<212> TYPE: DNA
<213> ORGANISM: Artificial Sequence
<220> FEATURE:
<223> OTHER INFORMATION: Consensus sequence for transcriptional factor
      GHF-5

<400> SEQUENCE: 40 wtatycat                                                                  8

<210> SEQ ID NO 41
<211> LENGTH: 8
<212> TYPE: DNA
<213> ORGANISM: Artificial Sequence
<220> FEATURE:
<223> OTHER INFORMATION: Consensus sequence for transcriptional factor
      GHF-7

<400> SEQUENCE: 41 wtatycat                                                                  8

<210> SEQ ID NO 42
<211> LENGTH: 15
<212> TYPE: DNA
```

```
<213> ORGANISM: Artificial Sequence
<220> FEATURE:
<223> OTHER INFORMATION: Consensus sequence for transcriptional factor
      GR
<221> NAME/KEY: misc_feature
<222> LOCATION: (1)...(15)
<223> OTHER INFORMATION: n = A,T,C or G

<400> SEQUENCE: 42
agaacannnt gttct                                                      15

<210> SEQ ID NO 43
<211> LENGTH: 18
<212> TYPE: DNA
<213> ORGANISM: Artificial Sequence
<220> FEATURE:
<223> OTHER INFORMATION: Consensus sequence for transcriptional factor
      H1TF2

<400> SEQUENCE: 43
gcaccaatca cagcgcgc                                                   18

<210> SEQ ID NO 44
<211> LENGTH: 19
<212> TYPE: DNA
<213> ORGANISM: Artificial Sequence
<220> FEATURE:
<223> OTHER INFORMATION: Consensus sequence for transcriptional factor
      H2RIIBP

<400> SEQUENCE: 44
tcaggtcaca gtgacctga                                                  19

<210> SEQ ID NO 45
<211> LENGTH: 13
<212> TYPE: DNA
<213> ORGANISM: Artificial Sequence
<220> FEATURE:
<223> OTHER INFORMATION: Consensus sequence for transcriptional factor
      H2TF2

<400> SEQUENCE: 45
tggggattcc cca                                                        13

<210> SEQ ID NO 46
<211> LENGTH: 7
<212> TYPE: DNA
<213> ORGANISM: Artificial Sequence
<220> FEATURE:
<223> OTHER INFORMATION: Consensus sequence for transcriptional factor
      H-APF-1

<400> SEQUENCE: 46 ctggraa                                                                7

<210> SEQ ID NO 47
<211> LENGTH: 9
<212> TYPE: DNA
<213> ORGANISM: Artificial Sequence
<220> FEATURE:
<223> OTHER INFORMATION: Consensus sequence for transcriptional factor
      HIF

<400> SEQUENCE: 47 ctacgtgct                                                              9

<210> SEQ ID NO 48
```

-continued

```
<211> LENGTH: 13
<212> TYPE: DNA
<213> ORGANISM: Artificial Sequence
<220> FEATURE:
<223> OTHER INFORMATION: Consensus sequence for transcriptional factor
      HNF-1
<221> NAME/KEY: misc_feature
<222> LOCATION: (1)...(13)
<223> OTHER INFORMATION: n = A,T,C or G

<400> SEQUENCE: 48
gttaatnatt aac                                                          13

<210> SEQ ID NO 49
<211> LENGTH: 13
<212> TYPE: DNA
<213> ORGANISM: Artificial Sequence
<220> FEATURE:
<223> OTHER INFORMATION: Consensus sequence for transcriptional factor
      vHNF-1
<221> NAME/KEY: misc_feature
<222> LOCATION: (1)...(13)
<223> OTHER INFORMATION: n = A,T,C or G

<400> SEQUENCE: 49
gttaatnatt aac                                                          13

<210> SEQ ID NO 50
<211> LENGTH: 11
<212> TYPE: DNA
<213> ORGANISM: Artificial Sequence
<220> FEATURE:
<223> OTHER INFORMATION: Consensus sequence for transcriptional factor
      HNF-3A

<400> SEQUENCE: 50
tattgayttw g                                                            11

<210> SEQ ID NO 51
<211> LENGTH: 11
<212> TYPE: DNA
<213> ORGANISM: Artificial Sequence
<220> FEATURE:
<223> OTHER INFORMATION: Consensus sequence for transcriptional factor
      HNF-3B

<400> SEQUENCE: 51
tattgayttw g                                                            11

<210> SEQ ID NO 52
<211> LENGTH: 11
<212> TYPE: DNA
<213> ORGANISM: Artificial Sequence
<220> FEATURE:
<223> OTHER INFORMATION: Consensus sequence for transcriptional factor
      HNF-3C

<400> SEQUENCE: 52
tattgayttw g                                                            11

<210> SEQ ID NO 53
<211> LENGTH: 12
<212> TYPE: DNA
<213> ORGANISM: Artificial Sequence
<220> FEATURE:
<223> OTHER INFORMATION: Consensus sequence for transcriptional factor
      HNF-4

<400> SEQUENCE: 53
```
kgcwargkyc ay                                                                12

<210> SEQ ID NO 54
<211> LENGTH: 15
<212> TYPE: DNA
<213> ORGANISM: Artificial Sequence
<220> FEATURE:
<223> OTHER INFORMATION: Consensus sequence for transcriptional factor
      HSF
<221> NAME/KEY: misc_feature
<222> LOCATION: (1)...(15)
<223> OTHER INFORMATION: n = A,T,C or G

<400> SEQUENCE: 54
ngaanngaan ngaan                                                             15

<210> SEQ ID NO 55
<211> LENGTH: 10
<212> TYPE: DNA
<213> ORGANISM: Artificial Sequence
<220> FEATURE:
<223> OTHER INFORMATION: Consensus sequence for transcriptional factor
      IAF

<400> SEQUENCE: 55
gccatctgct                                                                   10

<210> SEQ ID NO 56
<211> LENGTH: 8
<212> TYPE: DNA
<213> ORGANISM: Artificial Sequence
<220> FEATURE:
<223> OTHER INFORMATION: Consensus sequence for transcriptional factor
      IRBP

<400> SEQUENCE: 56 agtgcact                                                                      8

<210> SEQ ID NO 57
<211> LENGTH: 16
<212> TYPE: DNA
<213> ORGANISM: Artificial Sequence
<220> FEATURE:
<223> OTHER INFORMATION: Consensus sequence for transcriptional factor
      IREBF-1

<400> SEQUENCE: 57
cgggaaatgg aaactg                                                            16

<210> SEQ ID NO 58
<211> LENGTH: 6
<212> TYPE: DNA
<213> ORGANISM: Artificial Sequence
<220> FEATURE:
<223> OTHER INFORMATION: Consensus sequence for transcriptional factor
      IRF
<221> NAME/KEY: misc_feature
<222> LOCATION: (1)...(6)
<223> OTHER INFORMATION: n = A,T,C or G

<400> SEQUENCE: 58 aannga                                                                        6

<210> SEQ ID NO 59
<211> LENGTH: 10
<212> TYPE: DNA
<213> ORGANISM: Artificial Sequence

```
<220> FEATURE:
<223> OTHER INFORMATION: Consensus sequence for transcriptional factor
      ISGF1

<400> SEQUENCE: 59
ctttcagttt                                                           10

<210> SEQ ID NO 60
<211> LENGTH: 10
<212> TYPE: DNA
<213> ORGANISM: Artificial Sequence
<220> FEATURE:
<223> OTHER INFORMATION: Consensus sequence for transcriptional factor
      ISGF2

<400> SEQUENCE: 60
ctttctcttt                                                           10

<210> SEQ ID NO 61
<211> LENGTH: 10
<212> TYPE: DNA
<213> ORGANISM: Artificial Sequence
<220> FEATURE:
<223> OTHER INFORMATION: Consensus sequence for transcriptional factor
      ISGF3

<400> SEQUENCE: 61
gcttcagttt                                                           10

<210> SEQ ID NO 62
<211> LENGTH: 13
<212> TYPE: DNA
<213> ORGANISM: Artificial Sequence
<220> FEATURE:
<223> OTHER INFORMATION: Consensus sequence for transcriptional factor
      KBF-1

<400> SEQUENCE: 62
tggggattcc cca                                                       13

<210> SEQ ID NO 63
<211> LENGTH: 10
<212> TYPE: DNA
<213> ORGANISM: Artificial Sequence
<220> FEATURE:
<223> OTHER INFORMATION: Consensus sequence for transcriptional factor
      Ker1

<400> SEQUENCE: 63
gcctgcaggc                                                           10

<210> SEQ ID NO 64
<211> LENGTH: 13
<212> TYPE: DNA
<213> ORGANISM: Artificial Sequence
<220> FEATURE:
<223> OTHER INFORMATION: Consensus sequence for transcriptional factor
      LFB3
<221> NAME/KEY: misc_feature
<222> LOCATION: (1)...(13)
<223> OTHER INFORMATION: n = A,T,C or G

<400> SEQUENCE: 64
gttaatnatt aac                                                       13

<210> SEQ ID NO 65
<211> LENGTH: 15
```

-continued

```
<212> TYPE: DNA
<213> ORGANISM: Artificial Sequence
<220> FEATURE:
<223> OTHER INFORMATION: Consensus sequence for transcriptional factor
      LIT-1

<400> SEQUENCE: 65
gcgccctttg gacct                                                    15

<210> SEQ ID NO 66
<211> LENGTH: 9
<212> TYPE: DNA
<213> ORGANISM: Artificial Sequence
<220> FEATURE:
<223> OTHER INFORMATION: Consensus sequence for transcriptional factor
      LyF-1

<400> SEQUENCE: 66 rrtgggagr                                                            9

<210> SEQ ID NO 67
<211> LENGTH: 13
<212> TYPE: DNA
<213> ORGANISM: Artificial Sequence
<220> FEATURE:
<223> OTHER INFORMATION: Consensus sequence for transcriptional factor
      MBF-1

<400> SEQUENCE: 67
ytaaaaataa yyy                                                      13

<210> SEQ ID NO 68
<211> LENGTH: 7
<212> TYPE: DNA
<213> ORGANISM: Artificial Sequence
<220> FEATURE:
<223> OTHER INFORMATION: Consensus sequence for transcriptional factor
      MBF-I

<400> SEQUENCE: 68 tgcrcrc                                                              7

<210> SEQ ID NO 69
<211> LENGTH: 13
<212> TYPE: DNA
<213> ORGANISM: Artificial Sequence
<220> FEATURE:
<223> OTHER INFORMATION: Consensus sequence for transcriptional factor
      MBP-1

<400> SEQUENCE: 69
tggggattcc cca                                                      13

<210> SEQ ID NO 70
<211> LENGTH: 7
<212> TYPE: DNA
<213> ORGANISM: Artificial Sequence
<220> FEATURE:
<223> OTHER INFORMATION: Consensus sequence for transcriptional factor
      MCBF

<400> SEQUENCE: 70 cattcct                                                              7

<210> SEQ ID NO 71
<211> LENGTH: 10
<212> TYPE: DNA
```

```
<213> ORGANISM: Artificial Sequence
<220> FEATURE:
<223> OTHER INFORMATION: Consensus sequence for transcriptional factor
      MEF-2

<400> SEQUENCE: 71 ytawaaatar                                                                10

<210> SEQ ID NO 72
<211> LENGTH: 7
<212> TYPE: DNA
<213> ORGANISM: Artificial Sequence
<220> FEATURE:
<223> OTHER INFORMATION: Consensus sequence for transcriptional factor
      MEP-1
<221> NAME/KEY: misc_feature
<222> LOCATION: (1)...(7)
<223> OTHER INFORMATION: n = A,T,C or G

<400> SEQUENCE: 72 tgcrcnc                                                                    7

<210> SEQ ID NO 73
<211> LENGTH: 16
<212> TYPE: DNA
<213> ORGANISM: Artificial Sequence
<220> FEATURE:
<223> OTHER INFORMATION: Consensus sequence for transcriptional factor
      MR
<221> NAME/KEY: misc_feature
<222> LOCATION: (1)...(16)
<223> OTHER INFORMATION: n = A,T,C or G

<400> SEQUENCE: 73
agaacannnn tgttct                                                         16

<210> SEQ ID NO 74
<211> LENGTH: 6
<212> TYPE: DNA
<213> ORGANISM: Artificial Sequence
<220> FEATURE:
<223> OTHER INFORMATION: Consensus sequence for transcriptional factor
      Myb

<400> SEQUENCE: 74 yaackg                                                                     6

<210> SEQ ID NO 75
<211> LENGTH: 6
<212> TYPE: DNA
<213> ORGANISM: Artificial Sequence
<220> FEATURE:
<223> OTHER INFORMATION: Consensus sequence for transcriptional factor
      Myc

<400> SEQUENCE: 75 cacgtg                                                                     6

<210> SEQ ID NO 76
<211> LENGTH: 8
<212> TYPE: DNA
<213> ORGANISM: Artificial Sequence
<220> FEATURE:
<223> OTHER INFORMATION: Consensus sequence for transcriptional factor
      MyoD

<400> SEQUENCE: 76 caactgac                                                                   8
```

```
<210> SEQ ID NO 77
<211> LENGTH: 14
<212> TYPE: DNA
<213> ORGANISM: Artificial Sequence
<220> FEATURE:
<223> OTHER INFORMATION: Consensus sequence for transcriptional factor
      NF1
<221> NAME/KEY: misc_feature
<222> LOCATION: (1)...(14)
<223> OTHER INFORMATION: n = A,T,C or G

<400> SEQUENCE: 77
yggmnnnnng ccaa                                                       14

<210> SEQ ID NO 78
<211> LENGTH: 19
<212> TYPE: DNA
<213> ORGANISM: Artificial Sequence
<220> FEATURE:
<223> OTHER INFORMATION: Consensus sequence for transcriptional factor
      NF-AT

<400> SEQUENCE: 78
ggaggaaaaa ctgtttcat                                                  19

<210> SEQ ID NO 79
<211> LENGTH: 8
<212> TYPE: DNA
<213> ORGANISM: Artificial Sequence
<220> FEATURE:
<223> OTHER INFORMATION: Consensus sequence for transcriptional factor
      NF-E2

<400> SEQUENCE: 79 tgactcag                                                               8

<210> SEQ ID NO 80
<211> LENGTH: 8
<212> TYPE: DNA
<213> ORGANISM: Artificial Sequence
<220> FEATURE:
<223> OTHER INFORMATION: Consensus sequence for transcriptional factor
      NF-D

<400> SEQUENCE: 80 gatggcgg                                                               8

<210> SEQ ID NO 81
<211> LENGTH: 11
<212> TYPE: DNA
<213> ORGANISM: Artificial Sequence
<220> FEATURE:
<223> OTHER INFORMATION: Consensus sequence for transcriptional factor
      NF-GMa

<400> SEQUENCE: 81
grgrgttkca y                                                          11

<210> SEQ ID NO 82
<211> LENGTH: 7
<212> TYPE: DNA
<213> ORGANISM: Artificial Sequence
<220> FEATURE:
<223> OTHER INFORMATION: Consensus sequence for transcriptional factor
      NF-GMb

<400> SEQUENCE: 82
```

```
tcagrta                                                             7
```

```
<210> SEQ ID NO 83
<211> LENGTH: 9
<212> TYPE: DNA
<213> ORGANISM: Artificial Sequence
<220> FEATURE:
<223> OTHER INFORMATION: Consensus sequence for transcriptional factor
      NF-IL6
<221> NAME/KEY: misc_feature
<222> LOCATION: (1)...(9)
<223> OTHER INFORMATION: n = A,T,C or G

<400> SEQUENCE: 83 tknngnaak                                                           9
```

```
<210> SEQ ID NO 84
<211> LENGTH: 10
<212> TYPE: DNA
<213> ORGANISM: Artificial Sequence
<220> FEATURE:
<223> OTHER INFORMATION: Consensus sequence for transcriptional factor
      NFxB
<221> NAME/KEY: misc_feature
<222> LOCATION: (1)...(10)
<223> OTHER INFORMATION: n = A,T,C or G

<400> SEQUENCE: 84 gggamtnycc                                                          10
```

```
<210> SEQ ID NO 85
<211> LENGTH: 8
<212> TYPE: DNA
<213> ORGANISM: Artificial Sequence
<220> FEATURE:
<223> OTHER INFORMATION: Consensus sequence for transcriptional factor
      NF-W1

<400> SEQUENCE: 85 gttgcatc                                                            8
```

```
<210> SEQ ID NO 86
<211> LENGTH: 8
<212> TYPE: DNA
<213> ORGANISM: Artificial Sequence
<220> FEATURE:
<223> OTHER INFORMATION: Consensus sequence for transcriptional factor
      NF-W2

<400> SEQUENCE: 86 gttgcatc                                                            8
```

```
<210> SEQ ID NO 87
<211> LENGTH: 12
<212> TYPE: DNA
<213> ORGANISM: Artificial Sequence
<220> FEATURE:
<223> OTHER INFORMATION: Consensus sequence for transcriptional factor
      NGF1-B

<400> SEQUENCE: 87
aggtcatgac ct                                                       12
```

```
<210> SEQ ID NO 88
<211> LENGTH: 8
<212> TYPE: DNA
<213> ORGANISM: Artificial Sequence
```

```
<220> FEATURE:
<223> OTHER INFORMATION: Consensus sequence for transcriptional factor
      Oct-1

<400> SEQUENCE: 88 atgcaaat                                                                  8

<210> SEQ ID NO 89
<211> LENGTH: 8
<212> TYPE: DNA
<213> ORGANISM: Artificial Sequence
<220> FEATURE:
<223> OTHER INFORMATION: Consensus sequence for transcriptional factor
      Oct-2

<400> SEQUENCE: 89 atgcaaat                                                                  8

<210> SEQ ID NO 90
<211> LENGTH: 8
<212> TYPE: DNA
<213> ORGANISM: Artificial Sequence
<220> FEATURE:
<223> OTHER INFORMATION: Consensus sequence for transcriptional factor
      Oct-4

<400> SEQUENCE: 90 atgcwaat                                                                  8

<210> SEQ ID NO 91
<211> LENGTH: 8
<212> TYPE: DNA
<213> ORGANISM: Artificial Sequence
<220> FEATURE:
<223> OTHER INFORMATION: Consensus sequence for transcriptional factor
      Oct-6

<400> SEQUENCE: 91 atgcaaat                                                                  8

<210> SEQ ID NO 92
<211> LENGTH: 20
<212> TYPE: DNA
<213> ORGANISM: Artificial Sequence
<220> FEATURE:
<223> OTHER INFORMATION: Consensus sequence for transcriptional factor
      P53

<400> SEQUENCE: 92
rrrcwwgyyy rrrcwwgyyy                                                    20

<210> SEQ ID NO 93
<211> LENGTH: 23
<212> TYPE: DNA
<213> ORGANISM: Artificial Sequence
<220> FEATURE:
<223> OTHER INFORMATION: Consensus sequence for transcriptional factor
      Pax-1

<400> SEQUENCE: 93
caccgttccg ctctagatat ctc                                                23

<210> SEQ ID NO 94
<211> LENGTH: 14
<212> TYPE: DNA
<213> ORGANISM: Artificial Sequence
<220> FEATURE:
```

```
<223> OTHER INFORMATION: Consensus sequence for transcriptional factor
      PCF

<400> SEQUENCE: 94
agaaagggaa agga                                                         14

<210> SEQ ID NO 95
<211> LENGTH: 6
<212> TYPE: DNA
<213> ORGANISM: Artificial Sequence
<220> FEATURE:
<223> OTHER INFORMATION: Consensus sequence for transcriptional factor
      PEA3

<400> SEQUENCE: 95 aggaar                                                                   6

<210> SEQ ID NO 96
<211> LENGTH: 6
<212> TYPE: DNA
<213> ORGANISM: Artificial Sequence
<220> FEATURE:
<223> OTHER INFORMATION: Consensus sequence for transcriptional factor
      PPAR

<400> SEQUENCE: 96 aggtca                                                                   6

<210> SEQ ID NO 97
<211> LENGTH: 15
<212> TYPE: DNA
<213> ORGANISM: Artificial Sequence
<220> FEATURE:
<223> OTHER INFORMATION: Consensus sequence for transcriptional factor
      PR
<221> NAME/KEY: misc_feature
<222> LOCATION: (1)...(15)
<223> OTHER INFORMATION: n = A,T,C or G

<400> SEQUENCE: 97
agaacannnt gttct                                                        15

<210> SEQ ID NO 98
<211> LENGTH: 10
<212> TYPE: DNA
<213> ORGANISM: Artificial Sequence
<220> FEATURE:
<223> OTHER INFORMATION: Consensus sequence for transcriptional factor
      PRDI-BF1

<400> SEQUENCE: 98
aagtgaaagt                                                              10

<210> SEQ ID NO 99
<211> LENGTH: 18
<212> TYPE: DNA
<213> ORGANISM: Artificial Sequence
<220> FEATURE:
<223> OTHER INFORMATION: Consensus sequence for transcriptional factor
      PTF1
<221> NAME/KEY: misc_feature
<222> LOCATION: (1)...(18)
<223> OTHER INFORMATION: n = A,T,C or G

<400> SEQUENCE: 99 atgggganctc agctgtgc                                                    18
```

```
<210> SEQ ID NO 100
<211> LENGTH: 9
<212> TYPE: DNA
<213> ORGANISM: Artificial Sequence
<220> FEATURE:
<223> OTHER INFORMATION: Consensus sequence for transcriptional factor
      PU.I

<400> SEQUENCE: 100 agaggaact                                                                9

<210> SEQ ID NO 101
<211> LENGTH: 7
<212> TYPE: DNA
<213> ORGANISM: Artificial Sequence
<220> FEATURE:
<223> OTHER INFORMATION: Consensus sequence for transcriptional factor
      PuF

<400> SEQUENCE: 101 gggtggg                                                                  7

<210> SEQ ID NO 102
<211> LENGTH: 12
<212> TYPE: DNA
<213> ORGANISM: Artificial Sequence
<220> FEATURE:
<223> OTHER INFORMATION: Consensus sequence for transcriptional factor
      RAR

<400> SEQUENCE: 102
aggtcatgac ct                                                           12

<210> SEQ ID NO 103
<211> LENGTH: 16
<212> TYPE: DNA
<213> ORGANISM: Artificial Sequence
<220> FEATURE:
<223> OTHER INFORMATION: Consensus sequence for transcriptional factor
      RFX

<400> SEQUENCE: 103
cccctagcaa cagatg                                                       16

<210> SEQ ID NO 104
<211> LENGTH: 6
<212> TYPE: DNA
<213> ORGANISM: Artificial Sequence
<220> FEATURE:
<223> OTHER INFORMATION: Consensus sequence for transcriptional factor
      Runt

<400> SEQUENCE: 104 ygyggt                                                                   6

<210> SEQ ID NO 105
<211> LENGTH: 11
<212> TYPE: DNA
<213> ORGANISM: Artificial Sequence
<220> FEATURE:
<223> OTHER INFORMATION: Consensus sequence for transcriptional factor
      RVF

<400> SEQUENCE: 105
aagataaaac c                                                            11

<210> SEQ ID NO 106
```

```
<211> LENGTH: 6
<212> TYPE: DNA
<213> ORGANISM: Artificial Sequence
<220> FEATURE:
<223> OTHER INFORMATION: Consensus sequence for transcriptional factor
      RXR
<221> NAME/KEY: misc_feature
<222> LOCATION: (0)...(0)
<223> OTHER INFORMATION: in Direct Repeat Configuration

<400> SEQUENCE: 106 aggtca                                                                    6

<210> SEQ ID NO 107
<211> LENGTH: 6
<212> TYPE: DNA
<213> ORGANISM: Artificial Sequence
<220> FEATURE:
<223> OTHER INFORMATION: Consensus sequence for transcriptional factor
      SIF

<400> SEQUENCE: 107 cccgtm                                                                    6

<210> SEQ ID NO 108
<211> LENGTH: 9
<212> TYPE: DNA
<213> ORGANISM: Artificial Sequence
<220> FEATURE:
<223> OTHER INFORMATION: Consensus sequence for transcriptional factor
      Sp1

<400> SEQUENCE: 108 krggctrrk                                                                 9

<210> SEQ ID NO 109
<211> LENGTH: 9
<212> TYPE: DNA
<213> ORGANISM: Artificial Sequence
<220> FEATURE:
<223> OTHER INFORMATION: Consensus sequence for transcriptional factor
      SREBP1
<221> NAME/KEY: misc_binding
<222> LOCATION: (0)...(0)
<223> OTHER INFORMATION: E-Box consensus binding sequence

<400> SEQUENCE: 109 atcacgtga                                                                 9

<210> SEQ ID NO 110
<211> LENGTH: 10
<212> TYPE: DNA
<213> ORGANISM: Artificial Sequence
<220> FEATURE:
<223> OTHER INFORMATION: Consensus sequence for transcriptional factor
      SREBP1
<221> NAME/KEY: misc_binding
<222> LOCATION: (0)...(0)
<223> OTHER INFORMATION: non E-Box consensus    binding sequence

<400> SEQUENCE: 110
atcaccccac                                                               10

<210> SEQ ID NO 111
<211> LENGTH: 22
<212> TYPE: DNA
<213> ORGANISM: Artificial Sequence
<220> FEATURE:
<223> OTHER INFORMATION: Consensus sequence for transcriptional factor
```

```
      SRF

<400> SEQUENCE: 111
ggatgtccat attaggacat ct                                                22

<210> SEQ ID NO 112
<211> LENGTH: 9
<212> TYPE: DNA
<213> ORGANISM: Artificial Sequence
<220> FEATURE:
<223> OTHER INFORMATION: Consensus sequence for transcriptional factor
      STAT
<221> NAME/KEY: misc_feature
<222> LOCATION: (1)...(9)
<223> OTHER INFORMATION: n = A,T,C or G

<400> SEQUENCE: 112 ttcnnngaa                                                                9

<210> SEQ ID NO 113
<211> LENGTH: 12
<212> TYPE: DNA
<213> ORGANISM: Artificial Sequence
<220> FEATURE:
<223> OTHER INFORMATION: Consensus sequence for transcriptional factor
      T3R

<400> SEQUENCE: 113
aggtcatgac ct                                                           12

<210> SEQ ID NO 114
<211> LENGTH: 6
<212> TYPE: DNA
<213> ORGANISM: Artificial Sequence
<220> FEATURE:
<223> OTHER INFORMATION: Consensus sequence for transcriptional factor
      TBP

<400> SEQUENCE: 114 tataaa                                                                   6

<210> SEQ ID NO 115
<211> LENGTH: 5
<212> TYPE: DNA
<213> ORGANISM: Artificial Sequence
<220> FEATURE:
<223> OTHER INFORMATION: Consensus sequence for transcriptional factor
      TCF-1

<400> SEQUENCE: 115 mamag                                                                    5

<210> SEQ ID NO 116
<211> LENGTH: 8
<212> TYPE: DNA
<213> ORGANISM: Artificial Sequence
<220> FEATURE:
<223> OTHER INFORMATION: Consensus sequence for transcriptional factor
      TCF-2.alpha.

<400> SEQUENCE: 116 saggaagy                                                                 8

<210> SEQ ID NO 117
<211> LENGTH: 9
<212> TYPE: DNA
<213> ORGANISM: Artificial Sequence
```

```
<220> FEATURE:
<223> OTHER INFORMATION: Consensus sequence for transcriptional factor
      TEF-1

<400> SEQUENCE: 117 aagyatgca                                                                  9

<210> SEQ ID NO 118
<211> LENGTH: 8
<212> TYPE: DNA
<213> ORGANISM: Artificial Sequence
<220> FEATURE:
<223> OTHER INFORMATION: Consensus sequence for transcriptional factor
      TEF-2

<400> SEQUENCE: 118 gggtgtgg                                                                   8

<210> SEQ ID NO 119
<211> LENGTH: 10
<212> TYPE: DNA
<213> ORGANISM: Artificial Sequence
<220> FEATURE:
<223> OTHER INFORMATION: Consensus sequence for transcriptional factor
      TGT-3

<400> SEQUENCE: 119
aagtgtttgc                                                                10

<210> SEQ ID NO 120
<211> LENGTH: 10
<212> TYPE: DNA
<213> ORGANISM: Artificial Sequence
<220> FEATURE:
<223> OTHER INFORMATION: Consensus sequence for transcriptional factor
      TIN-1

<400> SEQUENCE: 120
aggaagttcc                                                                10

<210> SEQ ID NO 121
<211> LENGTH: 6
<212> TYPE: DNA
<213> ORGANISM: Artificial Sequence
<220> FEATURE:
<223> OTHER INFORMATION: Consensus sequence for transcriptional factor
      USF

<400> SEQUENCE: 121 cacgtg                                                                     6

<210> SEQ ID NO 122
<211> LENGTH: 9
<212> TYPE: DNA
<213> ORGANISM: Artificial Sequence
<220> FEATURE:
<223> OTHER INFORMATION: Consensus sequence for transcriptional factor
      WT-ZFP

<400> SEQUENCE: 122 cgcccccgc                                                                  9

<210> SEQ ID NO 123
<211> LENGTH: 15
<212> TYPE: DNA
<213> ORGANISM: Artificial Sequence
<220> FEATURE:
```

```
<223> OTHER INFORMATION: Consensus sequence for transcriptional factor
      XF1/2

<400> SEQUENCE: 123
tcttctcacg caact                                                    15

<210> SEQ ID NO 124
<211> LENGTH: 16
<212> TYPE: DNA
<213> ORGANISM: Artificial Sequence
<220> FEATURE:
<223> OTHER INFORMATION: Consensus sequence for transcriptional factor
      XPF-1
<221> NAME/KEY: misc_feature
<222> LOCATION: (1)...(16)
<223> OTHER INFORMATION: n = A,T,C or G

<400> SEQUENCE: 124
cacctgnnnn tttccc                                                   16

<210> SEQ ID NO 125
<211> LENGTH: 20
<212> TYPE: DNA
<213> ORGANISM: Artificial Sequence
<220> FEATURE:
<223> OTHER INFORMATION: Consensus sequence for transcriptional factor
      YB-1

<400> SEQUENCE: 125
atttttctga ttggccaaag                                               20

<210> SEQ ID NO 126
<211> LENGTH: 19
<212> TYPE: DNA
<213> ORGANISM: Artificial Sequence
<220> FEATURE:
<223> OTHER INFORMATION: Epstein-Barr Virus EBNA (B958 Strain) viral
      protein

<400> SEQUENCE: 126
ggttagcata tgctaacca                                                19

<210> SEQ ID NO 127
<211> LENGTH: 9
<212> TYPE: DNA
<213> ORGANISM: Artificial Sequence
<220> FEATURE:
<223> OTHER INFORMATION: Epstein-Barr Virus BZLF (B958 Strain) viral
      protein

<400> SEQUENCE: 127 ttagcaatg                                                            9

<210> SEQ ID NO 128
<211> LENGTH: 8
<212> TYPE: DNA
<213> ORGANISM: Artificial Sequence
<220> FEATURE:
<223> OTHER INFORMATION: Human CBF-1 (Epstein-Barr Virus cis-element)
      viral protein

<400> SEQUENCE: 128 cgtgggaa                                                             8

<210> SEQ ID NO 129
<211> LENGTH: 14
<212> TYPE: DNA
```

```
<213> ORGANISM: Artificial Sequence
<220> FEATURE:
<223> OTHER INFORMATION: Human Papilloma viral protein

<400> SEQUENCE: 129
accgaaaacg gtgt                                                       14

<210> SEQ ID NO 130
<211> LENGTH: 12
<212> TYPE: DNA
<213> ORGANISM: Artificial Sequence
<220> FEATURE:
<223> OTHER INFORMATION: Herpes simplex virus type 1 VP16 viral protein

<400> SEQUENCE: 130
atgctaatga ta                                                         12

<210> SEQ ID NO 131
<211> LENGTH: 60
<212> TYPE: DNA
<213> ORGANISM: Artificial Sequence
<220> FEATURE:
<223> OTHER INFORMATION: HIV TAT (TAR RNA Sequence) viral protein

<400> SEQUENCE: 131
gggtctctct ggttagacca gatctgagcc tgggagctct ctggctaact agggaaccca     60

<210> SEQ ID NO 132
<211> LENGTH: 19
<212> TYPE: DNA
<213> ORGANISM: Artificial Sequence
<220> FEATURE:
<223> OTHER INFORMATION: HIV Integrase viral protein

<400> SEQUENCE: 132
gtgtggaaaa tctctagca                                                  19

<210> SEQ ID NO 133
<211> LENGTH: 21
<212> TYPE: DNA
<213> ORGANISM: Artificial Sequence
<220> FEATURE:
<223> OTHER INFORMATION: P53 transcriptional factor consensus sequence
<221> NAME/KEY: misc_feature
<222> LOCATION: (1)...(21)
<223> OTHER INFORMATION: n = A,T,C or G

<400> SEQUENCE: 133
rrrcwwngyy yrrrcwwgyy y                                               21

<210> SEQ ID NO 134
<211> LENGTH: 22
<212> TYPE: DNA
<213> ORGANISM: Artificial Sequence
<220> FEATURE:
<223> OTHER INFORMATION: P53 transcriptional factor consensus sequence
<221> NAME/KEY: misc_feature
<222> LOCATION: (1)...(22)
<223> OTHER INFORMATION: n = A,T,C or G

<400> SEQUENCE: 134
rrrcwwnngy yyrrrcwwgy yy                                              22

<210> SEQ ID NO 135
<211> LENGTH: 23
<212> TYPE: DNA
<213> ORGANISM: Artificial Sequence
```

```
<220> FEATURE:
<223> OTHER INFORMATION: P53 transcriptional factor consensus sequence
<221> NAME/KEY: misc_feature
<222> LOCATION: (1)...(23)
<223> OTHER INFORMATION: n = A,T,C or G

<400> SEQUENCE: 135
rrrcwwnnng yyyrrrcwwg yyy                                             23

<210> SEQ ID NO 136
<211> LENGTH: 24
<212> TYPE: DNA
<213> ORGANISM: Artificial Sequence
<220> FEATURE:
<223> OTHER INFORMATION: P53 transcriptional factor consensus sequence
<221> NAME/KEY: misc_feature
<222> LOCATION: (1)...(24)
<223> OTHER INFORMATION: n = A,T,C or G

<400> SEQUENCE: 136 rrcwwnnnn gyyyrrrcww gyyy                                             24

<210> SEQ ID NO 137
<211> LENGTH: 25
<212> TYPE: DNA
<213> ORGANISM: Artificial Sequence
<220> FEATURE:
<223> OTHER INFORMATION: P53 transcriptional factor consensus sequence
<221> NAME/KEY: misc_feature
<222> LOCATION: (1)...(25)
<223> OTHER INFORMATION: n = A,T,C or G

<400> SEQUENCE: 137
rrrcwwnnnn ngyyyrrrcw wgyyy                                           25

<210> SEQ ID NO 138
<211> LENGTH: 26
<212> TYPE: DNA
<213> ORGANISM: Artificial Sequence
<220> FEATURE:
<223> OTHER INFORMATION: P53 transcriptional factor consensus sequence
<221> NAME/KEY: misc_feature
<222> LOCATION: (1)...(26)
<223> OTHER INFORMATION: n = A,T,C or G

<400> SEQUENCE: 138
rrrcwwnnnn nngyyyrrrc wwgyyy                                          26

<210> SEQ ID NO 139
<211> LENGTH: 27
<212> TYPE: DNA
<213> ORGANISM: Artificial Sequence
<220> FEATURE:
<223> OTHER INFORMATION: P53 transcriptional factor consensus sequence
<221> NAME/KEY: misc_feature
<222> LOCATION: (1)...(27)
<223> OTHER INFORMATION: n = A,T,C or G

<400> SEQUENCE: 139
rrrcwwnnnn nnngyyyrrr cwgyyy                                          27

<210> SEQ ID NO 140
<211> LENGTH: 28
<212> TYPE: DNA
<213> ORGANISM: Artificial Sequence
<220> FEATURE:
<223> OTHER INFORMATION: P53 transcriptional factor consensus sequence
<221> NAME/KEY: misc_feature
<222> LOCATION: (1)...(28)
```

```
<223> OTHER INFORMATION: n = A,T,C or G

<400> SEQUENCE: 140
rrrcwwnnnn nnnngyyyrr rcwwgyyy                                    28

<210> SEQ ID NO 141
<211> LENGTH: 29
<212> TYPE: DNA
<213> ORGANISM: Artificial Sequence
<220> FEATURE:
<223> OTHER INFORMATION: P53 transcriptional factor consensus sequence
<221> NAME/KEY: misc_feature
<222> LOCATION: (1)...(29)
<223> OTHER INFORMATION: n = A,T,C or G

<400> SEQUENCE: 141
rrrcwwnnnn nnnnngyyyr rrcwwgyyy                                   29

<210> SEQ ID NO 142
<211> LENGTH: 30
<212> TYPE: DNA
<213> ORGANISM: Artificial Sequence
<220> FEATURE:
<223> OTHER INFORMATION: P53 transcriptional factor consensus sequence
<221> NAME/KEY: misc_feature
<222> LOCATION: (1)...(30)
<223> OTHER INFORMATION: n = A,T,C or G

<400> SEQUENCE: 142
rrrcwwnnnn nnnnnngyyy rrrcwwgyyy                                  30

<210> SEQ ID NO 143
<211> LENGTH: 31
<212> TYPE: DNA
<213> ORGANISM: Artificial Sequence
<220> FEATURE:
<223> OTHER INFORMATION: P53 transcriptional factor consensus sequence
<221> NAME/KEY: misc_feature
<222> LOCATION: (1)...(31)
<223> OTHER INFORMATION: n = A,T,C or G

<400> SEQUENCE: 143
rrrcwwnnnn nnnnnnngyy yrrrcwwgyy y                                31

<210> SEQ ID NO 144
<211> LENGTH: 32
<212> TYPE: DNA
<213> ORGANISM: Artificial Sequence
<220> FEATURE:
<223> OTHER INFORMATION: P53 transcriptional factor consensus sequence
<221> NAME/KEY: misc_feature
<222> LOCATION: (1)...(32)
<223> OTHER INFORMATION: n = A,T,C or G

<400> SEQUENCE: 144
rrrcwwnnnn nnnnnnnngy yyrrrcwwgy yy                               32

<210> SEQ ID NO 145
<211> LENGTH: 34
<212> TYPE: DNA
<213> ORGANISM: Artificial Sequence
<220> FEATURE:
<223> OTHER INFORMATION: P53 transcriptional factor consensus sequence
<221> NAME/KEY: misc_feature
<222> LOCATION: (1)...(34)
<223> OTHER INFORMATION: n = A,T,C or G

<400> SEQUENCE: 145
```

```
rrrcwwnnnn nnnnnnnnng yyyrrrcwwg yyys                                      34
```

<210> SEQ ID NO 146
<211> LENGTH: 255
<212> TYPE: DNA
<213> ORGANISM: Artificial Sequence
<220> FEATURE:
<223> OTHER INFORMATION: CMV sequence

<400> SEQUENCE: 146

```
tggccaagcg gcctctgata accaagcctg aggttatcag tgtaatgaag cgccgcattg         60
aggagatctg catgaaggtc tttgcccagt acattctggg ggccgatcct ctgagagtct        120
gctctcctag tgtggatgac ctacgggcca tcgccgagga gtcagatgag gaagaggcta        180
ttgtagccta cactttggcc accgctggtg tcagctcctc tgattctctg gtgtcacccc        240
cagagtcccc tgtac                                                         255
```

<210> SEQ ID NO 147
<211> LENGTH: 22
<212> TYPE: DNA
<213> ORGANISM: Artificial Sequence
<220> FEATURE:
<223> OTHER INFORMATION: NFkB consensus sequence

<400> SEQUENCE: 147

```
agttgagggg actttcccag gc                                                  22
```

<210> SEQ ID NO 148
<211> LENGTH: 23
<212> TYPE: DNA
<213> ORGANISM: Artificial Sequence
<220> FEATURE:
<223> OTHER INFORMATION: CREB consensus sequence

<400> SEQUENCE: 148

```
attgcctgac gtcagagagc tag                                                 23
```

<210> SEQ ID NO 149
<211> LENGTH: 24
<212> TYPE: DNA
<213> ORGANISM: Artificial Sequence
<220> FEATURE:
<223> OTHER INFORMATION: AP-1 consensus sequence

<400> SEQUENCE: 149

```
ccgttccggc tgactcatca agcg                                                24
```

<210> SEQ ID NO 150
<211> LENGTH: 7
<212> TYPE: DNA
<213> ORGANISM: Artificial Sequence
<220> FEATURE:
<223> OTHER INFORMATION: Consenses sequence for transcriptional factor
      Myc

<400> SEQUENCE: 150

```
tctctta                                                                    7
```